US010286009B2

(12) United States Patent
Wirth, III et al.

(10) Patent No.: US 10,286,009 B2
(45) Date of Patent: May 14, 2019

(54) PLURIPOTENT STEM CELL-DERIVED OLIGODENDROCYTE PROGENITOR CELLS FOR THE TREATMENT OF SPINAL CORD INJURY

(71) Applicant: Asterias Biotherapeutics, Inc., Fremont, CA (US)

(72) Inventors: Edward D. Wirth, III, Mountain View, CA (US); Jane S. Lebkowski, Portola Valley, CA (US)

(73) Assignee: Asterias Biotherapeutics, Inc., Fremont, CA (US)

( * ) Notice: Subject to any disclaimer, the term of this patent is extended or adjusted under 35 U.S.C. 154(b) by 0 days.

(21) Appl. No.: 15/156,316

(22) Filed: May 16, 2016

(65) Prior Publication Data

US 2016/0331786 A1 Nov. 17, 2016

Related U.S. Application Data

(60) Provisional application No. 62/162,739, filed on May 16, 2015.

(51) Int. Cl.

| | |
|---|---|
| ***A61K 35/30*** | (2015.01) |
| ***A61K 31/436*** | (2006.01) |
| ***A61K 9/00*** | (2006.01) |
| ***C12N 5/079*** | (2010.01) |

(52) U.S. Cl.

CPC ............ *A61K 35/30* (2013.01); *A61K 9/0085* (2013.01); *A61K 31/436* (2013.01); *C12N 5/0622* (2013.01); *C12N 2506/02* (2013.01)

(58) Field of Classification Search

CPC .. A61K 31/436; A61K 2300/00; A61K 35/30; A61K 9/0085; A61K 31/439; A61K 31/64; A61K 31/00; A61K 31/195; A61K 31/198; A61K 31/4453; A61K 31/451; A61K 31/454; A61K 45/06; A61K 39/12; A61K 48/00; A61K 48/005; A61K 48/0075; A61K 9/0014; A61K 9/0019; C12N 2506/02; C12N 5/0622; C12N 2500/92; C12N 2501/11; C12N 2501/115; C12N 2501/385

See application file for complete search history.

(56) References Cited

U.S. PATENT DOCUMENTS

| | | | | |
|---|---|---|---|---|
| 6,280,718 B1 * | 8/2001 | Kaufman | C12N 5/0647 424/93.1 |
| 7,285,415 B2 | 10/2007 | Keirstead et al. | |
| 7,579,188 B2 | 8/2009 | Keirstead et al. | |
| 2010/0158878 A1 * | 6/2010 | Capela | C12N 5/0622 424/93.7 |
| 2010/0239541 A1 * | 9/2010 | Johe | A61K 35/30 424/93.7 |
| 2011/0059055 A1 * | 3/2011 | Goldman | C12N 5/0622 424/93.7 |
| 2013/0143805 A1 * | 6/2013 | Whittaker | A61K 38/18 514/7.6 |

OTHER PUBLICATIONS

Almad et al., "Oligodendrocyte Fate after Spinal Cord Injury," Neurotherapeutics 8(2): 262-273 (2011).
Anderson et al., "Acceptable benefits and risks associated with surgically improving arm function in individuals living with cervical spinal cord injury," Spinal Cord 47(4):334-338 (2009).
Anderson and Hall, "Pathophysiology of spinal cord trauma," Annals of Emergency Medicine 22(6):987-992 (1993).
Behrmann et. al., "Spinal Cord Injury Produced by Consistent Mechanical Displacement of the Cord in Rats: Behavioral and Histologic Analysis," J. Neurotrauma 9(3), 197-217 (1992).
Cao et al., "Transplantation of Ciliary Neurotrophic Factor-Expressing Adult Oligodendrocyte Precursor Cells Promotes Remyelination and Functional Recovery after Spinal Cord Injury," Journal of Neuroscience 30(8): 2989-3001 (2010).
Davies et. al., "Transplantation of Specific Human Astrocytes Promotes Functional Recovery After Spinal Cord Injury," PLoS One 6(3), e17328 (2011).
Doi et. al., "Prolonged Maturation Culture Favors a Reduction in the Tumorigenicity and the Dopaminergic Function of Human ESC-Derived Neural Cells in a Primate Model of Parkinson's Disease," Stem Cells 30(5), 935-945 (2012).
Douvaras et. al., "Efficient Generation of Myelinating Oligodendrocytes from Primary Progressive Multiple Sclerosis Patients by Induced Pluripotent Stem Cells," Stem Cell Rep. 3(2), 250-259 (2014).
Faulkner et. al., "Human Embryonic Stem Cell-Derived Oligodendrocyte Progenitors for the Treatment of Spinal Cord Injury," Transpl. Immunol. 15(2), 131-142 (2005).
Goldman, "Stem and Progenitor Cell-Based Therapy of the Human Central Nervous System," Nat. Biotechnol. 23(7), 862-871 (2005).
Gordon et. al., "Chemokines Influence the Migration and Fate of Neural Precursor Cells from the Young Adult and Middle-Aged Rat Subventricular Zone," Exp. Neurol. 233(1), 587-594 (2012).
Hatch et. al., "Derivation of High-Purity Oligodendroglial Progenitors," Methods Mol. Biol. 549, 59-75 (2009).
Hu et. al., "Differentiation of Human Oligodendrocytes from Pluripotent Stem Cells," Nat. Protoc. 4(11), 1614-1622 (2009).
Hu et. al., "Hepatocyte Growth Factor Enhances the Generation of High-Purity Oligodendrocytes from Human Embryonic Stem Cells," Differentiation 78(2-3), 177-184 (2009).
Hulsebosch et al., "Rodent model of chronic central pain after spinal cord contusion injury and effects of gabapentin," Journal of Neurotrauma 17(12):1205-1217 (2000).
Kakulas, "The applied neuropathology of human spinal cord injury," Spinal Cord 37(2):79-88 (1999).
Karimi-Abdolrezaee et. al., "Delayed Transplantation of Adult Neural Precursor Cells Promotes Remyelination and Functional Neurological Recovery After Spinal Cord Injury," J. Neurosci. 26(13), 3377-3389 (2006).
Keirstead et al. "Human Embryonic Stem Cell-Derived Oligodendrocyte Progenitor Cell Transplants Remyelinate and Restore Locomotion after Spinal Cord Injury," Journal of Neuroscience 25(19):4694-4705 (2005).

(Continued)

*Primary Examiner* — Deborah K Ware
(74) *Attorney, Agent, or Firm* — Krista P. Kauppinen

(57) ABSTRACT

The present disclosure provides methods and compositions for making and using pluripotent stem cell-derived oligodendrocyte progenitor cells.

10 Claims, 15 Drawing Sheets

(56) References Cited

OTHER PUBLICATIONS

Klimaschewski et. al., "Regulation of Clusterin Expression Following Spinal Cord Injury," Cell Tissue Res. 306(2), 209-216 (2001).
Kriks et. al., "Dopamine Neurons Derived from Human ES Cells Efficiently Engraft in Animal Models of Parkinson's Disease," Nature 480(7378), 547-551 (2011).
Lu et. al., "Long-Distance Axonal Growth from Human Induced Pluripotent Stem Cells After Spinal Cord Injury," Neuron 83(4), 789-796 (2014).
Ma et. al., "Oligodendrocyte Precursor Cells Differentially Expressing Nogo-A but Not Mag Are More Permissive to Neurite Outgrowth Than Mature Oligodendrocytes," Exp. Neurol. 217(1), 184-196 (2009).
Metz et. al., "Validation of the Weight-Drop Contusion Model in Rats: A Comparative Study of Human Spinal Cord Injury," J. Neurotrauma 17(1), 1-17 (2000).
Mitsui et. al., "Transplantation of Neuronal and Glial Restricted Precursors Into Contused Spinal Cord Improves Bladder and Motor Functions, Decreases Thermal Hypersensitivity, and Modifies Intraspinal Circuitry," J. Neurosci. 25(42), 9624-9636 (2005).
Nakamura et. al., "Transplantation of Embryonic Spinal Cord-Derived Neurospheres Support Growth of Supraspinal Projections and Functional Recovery After Spinal Cord Injury in the Neonatal Rat," J. Neurosci. Res 81(4), 457-468 (2005).
Nistor et al., "Human Embryonic Stem Cells Differentiate into Oligodendrocytes in High Purity and Myelinate After Spinal Cord Transplantation," Glia 49(3):385-396 (2005).
Noble et. al., "Precursor Cell Biology and the Development of Astrocyte Transplantation Therapies: Lessons from Spinal Cord Injury," Neurotherapeutics 8(4), 677-693 (2011).
Norenberg et al., "The Pathology of Human Spinal Cord Injury: Defining the Problems," Journal of Neurotrauma 21(4):429-440 (2004).
Nothias et. al., "Combined Effects of Neurotrophin Secreting Transplants, Exercise, and Serotonergic Drug Challenge Improve Function in Spinal Rats," Neurorehabil. Neural Repair 19(4), 296-312 (2005).
Priest et al., "Preclinical safety of human embryonic stem cell-derived oligodendrocyte progenitors supporting clinical trials in spinal cord injury," Regenerative Medicine 10(8):939-958 (2015).
Roy et. al., "Functional Engraftment of Human ES Cell-Derived Dopaminergic Neurons Enriched by Coculture with Telomerase-Immortalized Midbrain Astrocytes," Nat. Med. 12(11), 1259-1268 (2006).
Scheff et. al., "Experimental Modeling of Spinal Cord Injury: Characterization of a Force-Defined Injury Device," J. Neurotrauma 20(2), 179-193 (2003).
Sharp et. al., "Human Embryonic Stem Cell-Derived Oligodendrocyte Progenitor Cell Transplants Improve Recovery After Cervical Spinal Cord Injury," Stem Cells 28(1), 152-163 (2010).
Tang et. al., "Redirection of Doublecortin-Positive Cell Migration by Over-Expression of the Chemokines MCP-1, MIP-1α and Gro-α in the Adult Rat Brain," Neuroscience 260, 240-248 (2014).
Vadivelu et. al., "Ng2+ Progenitors Derived from Embryonic Stem Cells Penetrate Glial Scar and Promote Axonal Outgrowth Into White Matter After Spinal Cord Injury," Stem Cells Transl. Med. 4(4), 401-411 (2015).
Wang et. al., "ApoE Mimetic Ameliorates Motor Deficit and Tissue Damage in Rat Spinal Cord Injury," J. Neurosci. Res 92(7), 884-892 (2014).
Wirth, E. "Phase I Clinical Trial of Human Embryonic Stem Cell-Derived Oligodendrocyte Progenitors in Subjects with Neurologically Complete Thoracic Spinal Cord Injury: Results and Next Steps," American Spinal Injury Association (ASIA) 2014 Meeting, San Antonio, Texas, May 16, 2014. (Oral Presentation).
Wright et. al., "Novel Roles for Osteopontin and Clusterin in Peripheral Motor and Sensory Axon Regeneration." J. Neurosci. 34(5), 1689-1700 (2014).
Zhang et al., "Oligodendrocyte Progenitor Cells Derived from Human Embryonic Stem Cells Express Neurotrophic Factors," Stem Cells and Development 15(6):943-952 (2006).
Zhang et. al., "Role of Matrix Metalloproteinases and Therapeutic Benefits of Their Inhibition in Spinal Cord Injury," Neurotherapeutics 8(2), 206-220 (2011).

* cited by examiner

| Spiking Group | Total # Cells Injected | Total # hESCs Injected | # Mice with Teratomas /Total # Mice Examined |
|---|---|---|---|
| 100% hESCs | $2 \times 10^6$ | $2 \times 10^6$ | 20/30 |
| 50% H1 hESCs +50% AST-OPC1 | $2 \times 10^6$ | $1 \times 10^6$ | 21/30 |
| 10% H1 hESCs +90% AST-OPC1 | $2 \times 10^6$ | $2 \times 10^5$ | 4/31 |
| 5% H1 hESCs +95% AST-OPC1 | $2 \times 10^6$ | $1 \times 10^5$ | 0/12 |
| 1% H1 hESCs +99% AST-OPC1 | $2 \times 10^6$ | $2 \times 10^4$ | 0/36 |
| 100% AST-OPC1 | $2 \times 10^6$ | 0 | 0/128 |
| Vehicle | 0 | 0 | 0/30 |

H&E
hAlu
Ki67

H&E
hAlu
Ki67

H&E
hAlu
Ki67

H&E
hAlu
Ki67

FIGURE 9

| Marker | # of AST-OPC1 Lots Having the Designated % of Cells Positive for the Marker /# of AST-OPC1 Lots Examined | | | | | |
|---|---|---|---|---|---|---|
| | >70% Marker Positive | 30-70% Marker Positive | 10-30% Marker Positive | 1-10% Marker Positive | <1% Marker Positive | 0% Marker Positive |
| Olig1 | 70/78 | 3/78 | 0/78 | 1/78 | 1/78 | 3/78 |
| PDGFRα | 74/78 | 0/78 | 0/78 | 1/78 | 1/78 | 2/78 |
| Nestin | 60/65 | 2/65 | 1/65 | 1/65 | 0/65 | 1/65 |
| NG2 | 40/77 | 20/77 | 7/77 | 3/77 | 2/77 | 5/77 |
| GFAP | 0/72 | 0/72 | 4/72 | 38/72 | 29/72 | 1/72 |
| Sox 10 | 6/75 | 3/75 | 7/75 | 36/75 | 11/75 | 12/75 |
| βTubIII | 1/72 | 0/72 | 2/72 | 18/72 | 48/72 | 3/72 |
| SSEA4 | 0/76 | 0/76 | 0/76 | 10/76 | 60/76 | 6/76 |
| MSA | 0/57 | 0/57 | 5/57 | 16/57 | 34/57 | 2/57 |
| PAX6 | 2/69 | 1/69 | 2/69 | 16/69 | 20/69 | 28/69 |
| GATA4 | 0/17 | 0/17 | 0/17 | 5/17 | 5/17 | 7/17 |
| OCT4 | 0/5 | 0/5 | 0/5 | 0/5 | 3/5 | 2/5 |
| AFP | 0/57 | 0/57 | 0/57 | 0/57 | 1/57 | 56/57 |
| HNF3β | 0/15 | 0/15 | 0/15 | 0/15 | 0/15 | 15/15 |

FIGURE 10

| Secreted Factor | Concentration (pg/mL) | Putative Role in Neural Repair |
|---|---|---|
| Clusterin | 29803± 19584 | Stimulates axonal outgrowth of sensory neurons |
| | | Upregulated post-injury to aid clearance of misfolded proteins |
| MCP-1 | 10072±42 | Chemoattractant for neural precursor cells |
| | | Promotes glial differentiation by neural precursor cells |
| TIMP1 | 2835± 1795 | Inhibits matrix metalloproteinases and cell death after spinal cord injury |
| ApoE | 2584± 1097 | Inhibits neuronal cell death and microglial activation after spinal cord injury |
| TIMP2 | 1361±574 | Inhibits matrix metalloproteinases and cell death after spinal cord injury |

FIGURE 11

| Hematology (Levels) | Clinical Chemistry (Blood or Urine Levels) | Coagulation Times |
|---|---|---|
| Leukocytes | Sodium | Activated Partial Thromboplastin Time (APTT) |
| Erythrocytes | Potassium | Prothrombin Time |
| Hemoglobin | Chloride | |
| Hematocrit | Phosphorus | |
| Platelets | Calcium | |
| Reticulocytes | Alkaline Phosphatase | |
| Neutrophils | Bilirubin | |
| Lymphocytes | Gamma-Glutamyl Transferase (GGT) | |
| Monocytes | Aspartate Amino Transferase (AST) | |
| Eosinophils | Alanine Aminotrasferase (ALT) | |
| Basophils | Urea Nitrogen | |
| Large Unstained Cells | Sorbitol Dehydrogenase | |
| Erythrocyte Morphology | Creatinine | |
| Blood Cell Morphology | Total protein | |
| | Albumin | |
| | Globulin | |
| | Cholesterol | |
| | Glucose | |
| | Ketones | |
| | Urobilinogen | |
| | Urine Volume | |
| | Urine Specific Gravity | |
| | Urine pH | |

FIGURE 14

| | | Neurological Level | | Zone of Partial Preservation | |
|---|---|---|---|---|---|
| Subject | Visit | Right Side Sensory | Left Side Sensory | Right Side Sensory | Left Side Sensory |
| 1002 | Baseline | T6 | T6 | T7 | T7 |
| | Year 1 | T6 | T7 | T7 | T7 |
| | Year 2 | T6 | T6 | T7 | T7 |
| | Year 3 | T6 | T6 | T7 | T7 |
| 1003 | Baseline | T8 | T8 | T9 | T9 |
| | Year 1 | T8 | T8 | T10* | T10* |
| | Year 2 | T8 | T9 | T10 | T10 |
| 1101 | Baseline | T6 | T6 | T8 | T8 |
| | Year 1 | T6 | T6 | T8 | T8 |
| | Year 2 | T5 | T5 | T7 | T7 |
| 1203 | Baseline | T7 | T8 | T8 | T9 |
| | Year 1 | T7 | T8 | T9 | T10 |
| | Year 2 | T8 | T8 | T9 | T9 |
| 1204 | Baseline | T3 | T3 | T4 | T4 |
| | Year 1 | T4 | T4 | T6 | T5 |
| | Year 2 | T4 | T4 | T6 | T5 |

PLURIPOTENT STEM CELL-DERIVED OLIGODENDROCYTE PROGENITOR CELLS FOR THE TREATMENT OF SPINAL CORD INJURY

PRIORITY

This application claims priority to U.S. Provisional Patent Application No. 62/162,739, filed on May 16, 2015, the entire contents of which are hereby incorporated by reference.

FIELD

The present disclosure relates to the field of stem cell biology and oligodendrocyte progenitor cells. More specifically, the present disclosure relates to oligodendrocyte progenitor cell compositions and methods of using the same.

BACKGROUND

Over 12,000 Americans suffer a spinal cord injury (SCI) each year, and approximately 1.3 million people in the United States are estimated to be living with a spinal cord injury. Traumatic SCI most commonly impacts individuals in their 20s and 30s, resulting in a high-level of permanent disability in young and previously healthy individuals. Individuals with SCI not only have impaired limb function, but suffer from impaired bowel and bladder function, reduced sensation, spasticity, autonomic dysreflexia, thromboses, sexual dysfunction, increased infections, decubitus ulcers and chronic pain, which can each significantly impact quality of life, and can even be life threatening in some instances. The life expectancy of an individual suffering a cervical spinal cord injury at age 20 is 20-25 years lower than that of a similarly aged individual with no SCI (NSCISC Spinal Cord Injury Facts and Figures 2013).

The clinical effects of spinal cord injury vary with the site and extent of damage. The neural systems that may be permanently disrupted below the level of the injury not only involve loss of control of limb muscles and the protective roles of temperature and pain sensation, but impact the cardiovascular system, breathing, sweating, bowel control, bladder control, and sexual function (Anderson K D, Fridén J, Lieber R L. Acceptable benefits and risks associated with surgically improving arm function in individuals living with cervical spinal cord injury. *Spinal Cord.* 2009 April;47(4): 334-8.) These losses lead to a succession of secondary problems, such as pressure sores and urinary tract infections that, until modern medicine, were rapidly fatal. Spinal cord injury often removes those unconscious control mechanisms that maintain the appropriate level of excitability in neural circuitry of the spinal cord. As a result, spinal motoneurons can become spontaneously hyperactive, producing debilitating stiffness and uncontrolled muscle spasms or spasticity. This hyperactivity can also cause sensory systems to produce chronic neurogenic pain and paresthesias, unpleasant sensations including numbness, tingling, aches, and burning. In recent polls of spinal cord injury patients, recovery of ambulatory function was not the highest ranked function that these patients desired to regain, but in many cases, relief from the spontaneous hyperactivity sequelae was paramount (Anderson K D, Fridén J, Lieber R L. Acceptable benefits and risks associated with surgically improving arm function in individuals living with cervical spinal cord injury. *Spinal Cord.* 2009 April;47(4):334-38).

There are multiple pathologies observed in the injured spinal cord due to the injury itself and subsequent secondary effects due to edema, hemorrhage and inflammation (Kakulas B A. The applied neuropathology of human spinal cord injury. *Spinal Cord.* 1999 February;37(2):79-88). These pathologies include the severing of axons, demyelination, parenchymal cavitation and the production of ectopic tissue such as fibrous scar tissue, gliosis, and dystrophic calcification (Anderson D K, Hall E D. Pathophysiology of spinal cord trauma. *Ann Emerg Med.* 1993 June;22(6):987-92; Norenberg M D, Smith J, Marcillo A. The pathology of human spinal cord injury: defining the problems. *J. Neurotrauma.* 2004 April;21(4):429-40). Oligodendrocytes, which provide both neurotrophic factor and myelination support for axons are susceptible to cell death following SCI and therefore are an important therapeutic target (Almad A, Sahinkaya F R, Mctigue D M. Oligodendrocyte fate after spinal cord injury. *Neurotherapics* 2011 8(2): 262-73). Replacement of the oligodendrocyte population could both support the remaining and damaged axons and also remyelinate axons to promote electrical conduction (Cao Q, He Q, Wang Yet et al. Transplantation of ciliary neurotrophic factor-expressing adult oligodendrocyte precursor cells promotes remyelination and functional recovery after spinal cord injury. *J. Neurosci.* 2010 30(8): 2989-3001).

AST-OPC1 is a population of oligodendrocyte progenitor cells (OPCs) that are produced from human embryonic stem cells (hESCs) using a specific differentiation protocol (Nistor G I, Totoiu M O, Hague N, Carpenter M K, Keirstead H S. Human embryonic stem cells differentiate into oligodendrocytes in high purity and myelinate after spinal cord transplantation. *Glia.* 2005 February;49(3):385-96). AST-OPC1 has been characterized by the expression of several molecules that are associated with oligodendrocyte precursors, including Nestin and NG2. The cells are further characterized by their minimal or lack of expression of markers known to be present in other cell types, such as neurons, astrocytes, endoderm, mesoderm, and hESCs (Keirstead H S, Nistor G, Bernal G, Totoiu M, Cloutier F, Sharp K, Steward O. Human embryonic stem cell-derived oligodendrocyte progenitor cell transplants remyelinate and restore locomotion after spinal cord injury. *J Neurosci.* 2005 May 11;25(19):4694-705; Zhang Y W, Denham J, Thies R S. Oligodendrocyte progenitor cells derived from human embryonic stem cells express neurotrophic factors. *Stem Cells Dev.* 2006 December;15(6):943-52). In vitro, AST-OPC1 also produces diffusible factors that support neurite extension from sensory neurons (Zhang Y W, Denham J, Thies R S. Oligodendrocyte progenitor cells derived from human embryonic stem cells express neurotrophic factors. *Stem Cells Dev.* 2006 December;15(6):943-52).

Pluripotent stem cell-derived neural cells have been used by researchers to treat CNS injuries and disorders in animal models. However, there remain obstacles in the development of such therapies for clinical applications in humans. To date, there are no available therapies utilizing human pluripotent stem cell-derived differentiated cell populations for the treatment of acute spinal cord injury or other neurological conditions requiring CNS repair and/or remyelination.

SUMMARY

In various embodiments described herein, the present disclosure provides, inter alia, a population of oligodendrocyte progenitor cells (OPCs) derived from pluripotent stem cells and methods of generating the same for use in the treatment of acute spinal cord injury and other conditions affecting the CNS. The present disclosure also identifies and provides factors produced and secreted by the OPCs of the present disclosure that have capacity to augment neural repair. The present disclosure also provides methods and compositions for reducing spinal cord injury-induced parenchymal cavitation in a subject with a spinal cord injury.

In an embodiment, the present disclosure provides a container comprising a composition comprising a population of allogeneic human oligodendrocyte progenitor cells (OPCs) that are capable of engrafting at a spinal cord injury site of a human subject following implantation of a dose of the composition into the spinal cord injury site. In certain embodiments, the OPCs do not elicit a humoral or cellular immune response in the subject when the subject undergoes a low dose immunosuppressant regimen.

In certain embodiments, the OPCs are capable of remaining within the spinal cord injury site of the subject for a period of about 180 days or longer following implantation of a dose of the composition into the spinal cord injury site. In other embodiments, the OPCs are capable of remaining within the spinal cord injury site of the subject for a period of about 2 years or longer following implantation of a dose of the composition into the spinal cord injury site. In further embodiments, the OPCs are capable of remaining within the spinal cord injury site of the subject for a period of about 3 years or longer following implantation of a dose of the composition into the spinal cord injury site. In yet further embodiments, the OPCs are capable of remaining within the spinal cord injury site of the subject for a period of about 4 years or longer following implantation of a dose of the composition into the spinal cord injury site.

In certain embodiments, the OPCs are capable of forming a tissue matrix in the spinal cord injury site, thereby reducing spinal cord injury-induced parenchymal cavitation. In certain embodiments, the OPCs are capable of forming a tissue matrix in the spinal cord injury site within about 180 days or less.

In certain embodiments, the OPCs are capable of secreting one or more biological factors. In certain embodiments, the biological factors secreted by the OPCs of the present disclosure may promote, without limitation, neural repair, axonal outgrowth and/or glial differentiation. In some embodiments, the OPCs are capable of secreting one or more of the factors selected from MCP-1, Clusterin, ApoE, TIMP1 and TIMP2. In further embodiments the OPCs are capable of secreting MCP-1 and one or more factors selected from: Clusterin, ApoE, TIMP1 and TIMP2. In yet further embodiments, the OPCs are capable of secreting all of the factors MCP-1, Clusterin, ApoE, TIMP1 and TIMP2.

In certain embodiments, the present disclosure provides a container comprising a composition comprising a population of allogeneic oligodendrocyte progenitor cells (OPCs) that are capable of engrafting at a spinal cord injury site of a human subject following implantation of a dose of the composition into the spinal cord injury site, wherein the dose of the composition comprises between about $2\times10^6$ and about $50\times10^6$ AST-OPC1. In some embodiments, the dose of the composition comprises about $50\times10^6$ AST-OPC1. In some embodiments, the dose of the composition comprises about $40\times10^6$ AS T-OPC1. In some embodiments, the dose of the composition comprises about $30\times10^6$ AS T-OPC1. In some embodiments, the dose of the composition comprises about $20\times10^6$ AST-OPC1. In some embodiments, the dose of the composition comprises about $10\times10^6$ AST-OPC1. In some embodiments, the dose of the composition comprises about $5\times10^6$ AST-OPC1. In some embodiments, the dose of the composition comprises about $2\times10^6$ AST-OPC1.

In certain embodiments, the present disclosure provides a container comprising a composition comprising a population of allogeneic oligodendrocyte progenitor cells (OPCs) that are capable of presenting at a spinal cord injury site of a subject and are capable of producing no detectable systemic toxicity in the subject following implantation of a dose of the composition into the spinal cord injury site. In certain embodiments, the OPCs do not induce significant alterations in a hematology, coagulation, urinalysis or clinical chemistry parameter of the subject.

In yet other embodiments, the present disclosure provides a method of reducing spinal cord injury-induced parenchymal cavitation in a human subject with an acute spinal cord injury, the method comprising administering to said subject a composition that comprises a population of allogeneic oligodendrocyte progenitor cells (OPCs) that are capable of engrafting at a spinal cord injury site. In certain embodiments, administering the composition comprises directly injecting the composition into the spinal cord injury site approximately 5 mm caudal of the spinal cord injury epicenter. In certain embodiments, the method further comprises administering to the subject a low dose immunosuppressant regimen. In certain embodiments, the immunosuppressant regimen comprises a dose of tacrolimus at about 0.03 mg/kg/day per os, adjusted to maintain a trough blood concentration of about 3-7 ng/mL through about day 46 following the administering of the composition, followed by tapering off and discontinuing the immunosuppressant at about day 60 following the administering of the composition comprising a population of allogeneically derived OPCs. In certain embodiments, the OPCs are capable of remaining within the spinal cord injury site of said subject for a period of about 180 days or longer following the administration of the composition to the spinal cord injury site. In certain embodiments, the OPCs are capable of remaining within the spinal cord injury site of said subject for a period of about 2 years or longer following the administration of the composition to the spinal cord injury site. In further embodiments the OPCs are capable of forming a tissue matrix in the spinal cord injury site of said subject within about 180 days or less, thereby reducing spinal cord injury-induced parenchymal cavitation. In certain embodiments, the subject has a thoracic spinal cord injury. In other embodiments, the subject has a cervical spinal cord injury. In certain embodiments, the composition comprises between about $2\times10^6$ to about $50\times10^6$ AST-OPC1 cells.

In additional embodiments, the present disclosure provides methods of characterizing and verifying the purity of the OPCs of the present disclosure based on their marker expression profile. In other embodiments, the present disclosure provides compositions and methods for stimulating axonal outgrowth in vitro using the OPCs of the present disclosure. In yet other embodiments, the present disclosure provides compositions and methods for stimulating axon myelination in vivo using the OPCs of the present disclosure. In further embodiments, the present disclosure provides methods for evaluating the safety and toxicity of the OPCs of the present disclosure in preclinical studies using rodent models of dysmyelination and contusion injury. In yet other embodiments, the present disclosure provides compositions and methods for administering OPCs to human subjects with a spinal cord injury. In other embodiments, the present disclosure provides compositions and methods for testing the safety and efficacy of administering OPCs to human subjects with a spinal cord injury.

In additional embodiments, the present disclosure provides a population of oligodendrocyte progenitor cells (OPCs) that are the in vitro differentiated progeny of pluripotent stem cells and that are suitable for administering to a subject with a spinal cord injury. In certain embodiments, the population of OPCs are the in vitro differentiated progeny of human embryonic stem cells. In certain embodiments, the oligodendrocyte progenitor cells express one or more markers selected from: Nestin, Olig1, PDGF-Rα and NG2. In some embodiments, at least 70% of the cells in the OPC population are positive for Nestin expression. In other embodiments, at least 30% of the cells in the OPC population are positive for NG2 expression.

In additional embodiments, the present disclosure provides a method for treating a subject in need of therapy, comprising administering to the subject a population of OPCs that are the in vitro differentiated progeny of pluripotent stem cells. In some embodiments, the method for treating a subject in need of therapy comprises administering to the subject a population of OPCs that are the in vitro differentiated progeny of human embryonic stem cells. In some embodiments, the subject in need of therapy has a defect or injury requiring myelin repair or remyelination. In some embodiments, the subject in need of therapy has a spinal cord injury. In some embodiments, the subject in need of therapy is human.

In another embodiment, the present disclosure provides a pharmaceutical composition comprising a population of oligodendrocyte progenitor cells that are the in vitro differentiated progeny of pluripotent stem cells and a biologically acceptable carrier or delivery system.

BRIEF DESCRIPTION OF DRAWINGS

For a fuller understanding of the nature and advantages of the present invention, reference should be had to the following detailed description taken in connection with the accompanying drawings.

FIG. 9 depicts phenotypic marker expression of AST-OPC1 as assessed by immunocytochemistry.

FIG. 10 depicts factors secreted by AST-OPC1 with putative roles in neuronal repair.

FIG. 11 depicts physiological parameters examined to assess the potential systemic toxicity of AST-OPC1.

FIG. 14 depicts a summary of sensory neurological function in the 5 clinical trial subjects from the baseline/beginning of clinical trial through year 2 (year 3 for one subject).

DETAILED DESCRIPTION

Figure 1A:
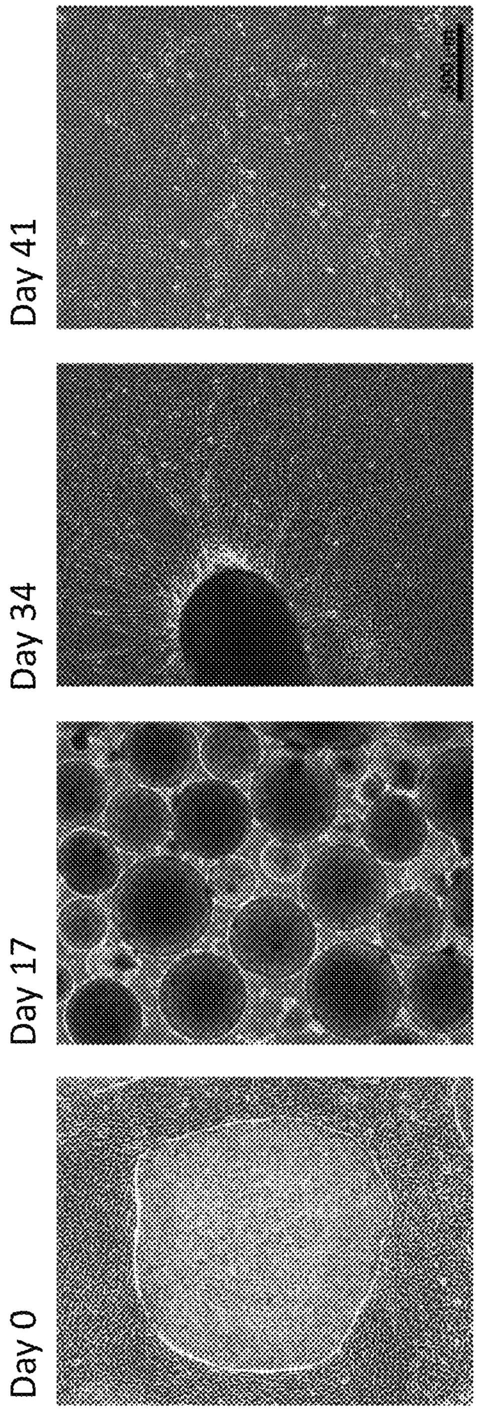
FIG. 1A consists of bright-field photomicrographs of differentiation of human embryonic stem cells into AST-OPC1 over 41 days.

Before the present compositions and methods are described, it is to be understood that the present disclosure is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular aspects of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the disclosure.

All publications, patent applications, patents and other references cited herein are incorporated by reference in their entireties.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

Methods disclosed herein can comprise one or more steps or actions for achieving the described method. The method steps and/or actions may be interchanged with one another without departing from the scope of the present invention. In other words, unless a specific order of steps or actions is required for proper operation of the embodiment, the order and/or use of specific steps and/or actions may be modified without departing from the scope of the present invention.

As used in the description of the disclosure and the appended claims, the singular forms “a,” “an” and “the” are intended to include the plural forms as well, unless the context clearly indicates otherwise.

As used herein, “and/or” refers to and encompasses any and all possible combinations of one or more of the associated listed items, as well as the lack of combinations when interpreted in the alternative (“or”).

The terms “about” and “approximately” as used herein when referring to a measurable value such as a percentages, density, volume and the like, is meant to encompass variations of ±20%, ±10%, ±5%, ±1%, ±0.5%, or even ±0.1% of the specified amount.

As used herein, phrases such as “between X and Y” and “between about X and Y” should be interpreted to include X and Y. As used herein, phrases such as “between about X and Y” mean “between about X and about Y” and phrases such as “from about X to Y” mean “from about X to about Y.”

The term “AST-OPC1” refers to a specific, characterized, in vitro differentiated cell population containing a mixture of oligodendrocyte progenitor cells (OPCs) and other characterized cell types obtained from undifferentiated human embryonic stem cells (uhESCs) according to specific differentiation protocols disclosed herein.

Compositional analysis of AST-OPC1 by immunocytochemistry (ICC), flow cytometry, and quantitative polymerase chain reaction (qPCR) demonstrates that the cell population is comprised primarily of neural lineage cells of the oligodendrocyte phenotype. Other neural lineage cells, namely astrocytes and neurons, are present at low frequencies. The only non-neural cells detected in the population are epithelial cells. Mesodermal, endodermal lineage cells and uhESCs are routinely below quantitation or detection of the assays.

The term “oligodendrocyte progenitor cells” (OPCs), as used herein, refers to cells of neuroectoderm/glial lineage having the characteristics of a cell type found in the central nervous system, capable of differentiating into oligodendrocytes. These cells typically express the characteristic markers Nestin, NG2 and PDGF-Rα.

The terms “treatment,” “treat” “treated,” or “treating,” as used herein, can refer to both therapeutic treatment or prophylactic or preventative measures, wherein the object is to prevent or slow down (lessen) an undesired physiological condition, symptom, disorder or disease, or to obtain beneficial or desired clinical results. In some embodiments, the term may refer to both treating and preventing. For the purposes of this disclosure, beneficial or desired clinical results may include, but are not limited to one or more of the following: alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response. Treatment also includes prolonging survival as compared to expected survival if not receiving treatment.

The term “subject,” as used herein includes, but is not limited to, humans, non-human primates and non-human vertebrates such as wild, domestic and farm animals including any mammal, such as cats, dogs, cows, sheep, pigs, horses, rabbits, rodents such as mice and rats. In some embodiments, the term “subject,” refers to a male. In some embodiments, the term “subject,” refers to a female.

As used herein, “implantation” or “transplantation” refers to the administration of a cell population into a target tissue using a suitable delivery technique, (e.g., using an injection device).

As used herein, "engraftment" and "engrafting" refer to incorporation of implanted tissue or cells (i.e. "graft tissue" or "graft cells") into the body of a subject. The presence of graft tissue or graft cells at or near the implantation site 180 days or later, post implantation, is indicative of engraftment. In certain embodiments, imaging techniques (such as, e.g. MRI imaging), can be used to detect the presence of graft tissue.

As used herein, "allogeneic" and "allogeneically derived" refer to cell populations derived from a source other than the subject and hence genetically non-identical to the subject. In certain embodiments, allogeneic cell populations are derived from cultured pluripotent stem cells. In certain embodiments, allogeneic cell populations are derived from hESCs. In other embodiments, allogeneic cell populations are derived from induced pluripotent stem (iPS) cells. In yet other embodiments, allogeneic cell populations are derived from primate pluripotent (pPS) cells.

As used herein, "parenchymal cavitation" refers to formation of a lesion or cavity within a CNS injury site or proximate to a CNS injury site, in an area normally occupied by parenchymal CNS tissue. The cavities or lesions can be filled with extracellular fluid and may contain macrophages, small bands of connective tissue and blood vessels.

The terms "central nervous system" and "CNS" as used interchangeably herein refer to the complex of nerve tissues that control one or more activities of the body, which include but are not limited to, the brain and the spinal cord in vertebrates.

Propagation and Culture of Undifferentiated Pluripotent Stem Cells

In certain embodiments, the present disclosure provides methods to produce large numbers of highly pure, characterized oligodendrocyte progenitor cells from pluripotent stem cells. Derivation of oligodendrocyte progenitor cells (OPCs) from pluripotent stem cells according to the methods of the invention provides a renewable and scalable source of OPCs for a number of important therapeutic, research, development, and commercial purposes, including treatment of acute spinal cord injury.

Methods of propagation and culture of undifferentiated pluripotent stem cells have been previously described. With respect to tissue and cell culture of pluripotent stem cells, the reader may wish to refer to any of numerous publications available in the art, e.g., *Teratocarcinomas and Embryonic Stem cells: A Practical Approach* (E. J. Robertson, Ed., IRL Press Ltd. 1987); *Guide to Techniques in Mouse Development* (P. M. Wasserman et al., Eds., Academic Press 1993); *Embryonic Stem Cell Differentiation in Vitro* (M. V. Wiles, Meth. Enzymol. 225:900, 1993); *Properties and Uses of Embryonic Stem Cells: Prospects for Application to Human Biology and Gene Therapy* (P. D. Rathjen et al., Reprod. Fertil. Dev. 10:31, 1998; and R. I. Freshney, Culture of Animal Cells, Wiley-Liss, New York, 2000).

In certain embodiments, a method can be carried out on a pluripotent stem cell line. In other embodiments, a method can be carried out on an embryonic stem cell line. In an embodiment, a method can be carried out on a plurality of undifferentiated stem cells that are derived from an H1, H7, H9, H13, or H14 cell line. In another embodiment, undifferentiated stem cells can be derived from an induced pluripotent stem cell (iPS) line. In another embodiment, a method can be carried out on a primate pluripotent stem (pPS) cell line. In yet another embodiment, undifferentiated stem cells can be derived from parthenotes, which are embryos stimulated to produce hESCs without fertilization.

In one embodiment, undifferentiated pluripotent stem cells can be maintained in an undifferentiated state without added feeder cells (see, e.g., (2004) Rosler et al., *Dev. Dynam.* 229:259). Feeder-free cultures are typically supported by a nutrient medium containing factors that promote proliferation of the cells without differentiation (see, e.g., U.S. Pat. No. 6,800,480). In one embodiment, conditioned media containing such factors can be used. Conditioned media can be obtained by culturing the media with cells secreting such factors. Suitable cells include, but are not limited to, irradiated (~4,000 Rad) primary mouse embryonic fibroblasts, telomerized mouse fibroblasts, or fibroblast-like cells derived from pPS cells (U.S. Pat. No. 6,642,048). Medium can be conditioned by plating the feeders in a serum free medium, such as knock-out DMEM supplemented with 20% serum replacement and 4 ng/mL bFGF. Medium that has been conditioned for 1-2 days can be supplemented with further bFGF, and used to support pPS cell culture for 1-2 days (see. e.g., WO 01/51616; Xu et al., (2001) *Nat. Biotechnol.* 19:971).

Alternatively, fresh or non-conditioned medium can be used, which has been supplemented with added factors (such as, e.g., a fibroblast growth factor or forskolin) that promote proliferation of the cells in an undifferentiated form. Non-limiting examples include a base medium like X-VIVO™ 10 (Lonza, Walkersville, Md.) or QBSF™-60 (Quality Biological Inc. Gaithersburg, Md.), supplemented with bFGF at 40-80 ng/mL, and optionally containing SCF (15 ng/mL), or Ft3 ligand (75 ng/mL) (see, e.g., Xu et al., (2005) *Stem Cells* 23(3):315). These media formulations have the advantage of supporting cell growth at 2-3 times the rate in other systems (see, e.g., WO 03/020920). In one embodiment, undifferentiated pluripotent cells such as hESCs, can be cultured in a media comprising bFGF and TGFβ. Non-limiting example concentrations of bFGF include about 80 ng/ml. Non-limiting example concentrations of TGFβ include about 0.5 ng/ml.

In one embodiment, undifferentiated pluripotent cells can be cultured on a layer of feeder cells, typically fibroblasts derived from embryonic or fetal tissue (Thomson et al. (1998) *Science* 282:1145). Feeder cells can be derived, inter alia, from a human or a murine source. Human feeder cells can be isolated from various human tissues, or can be derived via differentiation of human embryonic stem cells into fibroblast cells (see, e.g., WO 01/51616). In one embodiment, human feeder cells that can be used include, but are not limited to, placental fibroblasts (see, e.g., Genbacev et al. (2005) *Fertil. Steril.* 83(5):1517), fallopian tube epithelial cells (see, e.g., Richards et al. (2002) *Nat. Biotechnol.,* 20:933), foreskin fibroblasts (see, e.g., Amit et al. (2003) *Biol. Reprod.*68:2150), and uterine endometrial cells (see, e.g., Lee et al. (2005) *Biol. Reprod.* 72(1):42).

Various solid surfaces can be used in the culturing of undifferentiated pluripotent cells. Those solid surfaces include, but are not limited to, standard commercially available cell culture plates, such as 6-well, 24-well, 96-well, or 144-well plates. Other solid surfaces include, but are not limited to, microcarriers and disks. Solid surfaces suitable for growing undifferentiated pluripotent cells can be made of a variety of substances including, but not limited to, glass or plastic such as polystyrene, polyvinylchloride, polycarbonate, polytetrafluorethylene, melinex, thermanox, or combinations thereof. In one embodiment, suitable surfaces can comprise one or more polymers, such as, e.g., one or more acrylates. In one embodiment, a solid surface can be three-dimensional in shape. Non-limiting examples of three-dimensional solid surfaces are described, e.g., in U.S. Patent Pub. No. 2005/0031598.

In one embodiment, undifferentiated stem cells can be grown under feeder-free conditions on a growth substrate. In one embodiment, a growth substrate can be Matrigel® (e.g., Matrigel® or Matrigel® GFR), recombinant Laminin, or Vitronectin. In another embodiment, undifferentiated stem cells can be subcultured using various methods such as using collagenase, or such as manual scraping. In another embodiment, undifferentiated stem cells can be subcultured using non-enzymatic means, such as 0.5 mM EDTA in PBS, or such as using ReLeSR™. In an embodiment, a plurality of undifferentiated stem cells are seeded or subcultured at a seeding density that allows the cells to reach confluence in about three to about ten days. In an embodiment, the seeding density can range from about $6.0\times10^3$ cells/cm$^2$ to about $5.0\times10^5$ cells/cm$^2$, such as about $1.0\times10^4$ cells/cm$^2$, such as about $5.0\times10^4$ cells/cm$^2$, such as about $1.0\times10^5$ cells/cm$^2$, or such as about $3.0\times10^5$ cells/cm$^2$ of growth surface. In another embodiment, the seeding density can range from about $6.0\times10^3$ cells/cm$^2$ to about $1.0\times10^4$ cells/cm$^2$ of growth surface, such as about $6.0\times10^3$ cells/cm$^2$ to about $9.0\times10^3$ cells/cm$^2$, such as about $7.0\times10^3$ cells/cm$^2$ to about $1.0\times10^4$ cells/cm$^2$, such as about $7.0\times10^3$ cells/cm$^2$ to about $9.0\times10^3$ cells/cm$^2$, or such as about $7.0\times10^3$ cells/cm$^2$ to about $8.0\times10^3$ cells/cm$^2$ of growth surface. In yet another embodiment the seeding density can range from about $1.0\times10^4$ cells/cm$^2$ to about $1.0\times10^5$ cells/cm$^2$ of growth surface, such as about $2.0\times10^4$ cells/cm$^2$ to about $9.0\times10^4$ cells/cm$^2$, such as about $3.0\times10^4$ cells/cm$^2$ to about $8.0\times10^4$ cells/cm$^2$, such as about $4.0\times10^4$ cells/cm$^2$ to about $7.0\times10^4$ cells/cm$^2$, or such as about $5.0\times10^4$ cells/cm$^2$ to about $6.0\times10^4$ cells/cm$^2$ of growth surface. In an embodiment, the seeding density can range from about $1.0\times10^5$ cells/cm$^2$ to about $5.0\times10^5$ cells/cm$^2$ of growth surface, such as about $1.0\times10^5$ cells/cm$^2$ to about $4.5\times10^5$ cells/cm$^2$, such as about $1.5\times10^5$ cells/cm$^2$ to about $4.0\times10^5$ cells/cm$^2$, such as about $2.0\times10^5$ cells/cm$^2$ to about $3.5\times10^5$ cells/cm$^2$, or such as about $2.5\times10^5$ cells/cm$^2$ to about $3.0\times10^5$ cells/cm$^2$ of growth surface.

Any of a variety of suitable cell culture and sub-culturing techniques can be used to culture cells in accordance with the present disclosure. For example, in one embodiment, a culture medium can be exchanged at a suitable time interval. In one embodiment, a culture medium can be completely exchanged daily, initiating about 2 days after sub-culturing of the cells. In another embodiment, when a culture reaches about 90% colony coverage, a surrogate flask can be sacrificed and enumerated using one or more suitable reagents, such as, e.g., Collagenase IV and 0.05% Trypsin-EDTA in series to achieve a single cell suspension for quantification. In an embodiment, a plurality undifferentiated stem cells can then be sub-cultured before seeding the cells on a suitable growth substrate (e.g., Matrigel® GFR) at a seeding density that allows the cells to reach confluence over a suitable period of time, such as, e.g., in about three to ten days. In one embodiment, undifferentiated stem cells can be subcultured using Collagenase IV and expanded on a recombinant laminin matrix. In one embodiment, undifferentiated stem cells can be subcultured using Collagenase IV and expanded on a Matrigel® matrix. In one embodiment, undifferentiated stem cells can be subcultured using ReLeSR™ and expanded on a Vitronectin matrix.

In one embodiment, the seeding density can range from about $6.0\times10^3$ cells/cm$^2$ to about $5.0\times10^5$ cells/cm$^2$, such as about $1.0\times10^4$ cells/cm$^2$, such as about $5.0\times10^4$ cells/cm$^2$, such as about $1.0\times10^5$ cells/cm$^2$, or such as about $3.0\times10^5$ cells/cm$^2$ of growth surface. In another embodiment, the seeding density can range from about $6.0\times10^3$ cells/cm$^2$ to about $1.0\times10^4$ cells/cm$^2$ of growth surface, such as about $6.0\times10^3$ cells/cm$^2$ to about $9.0\times10^3$ cells/cm$^2$, such as about $7.0\times10^3$ cells/cm$^2$ to about $1.0\times10^4$ cells/cm$^2$, such as about $7.0\times10^3$ cells/cm$^2$ to about $9.0\times10^3$ cells/cm$^2$, or such as about $7.0\times10^3$ cells/cm$^2$ to about $8.0\times10^3$ cells/cm$^2$ of growth surface. In yet another embodiment, the seeding density can range from about $1.0\times10^4$ cells/cm$^2$ to about $1.0\times10^5$ cells/cm$^2$ of growth surface, such as about $2.0\times10^4$ cells/cm$^2$ to about $9.0\times10^4$ cells/cm$^2$, such as about $3.0\times10^4$ cells/cm$^2$ to about $8.0\times10^4$ cells/cm$^2$, such as about $4.0\times10^4$ cells/cm$^2$ to about $7.0\times10^4$ cells/cm$^2$, or such as about $5.0\times10^4$ cells/cm$^2$ to about $6.0\times10^4$ cells/cm$^2$ of growth surface. In an embodiment, the seeding density can range from about $1.0\times10^5$ cells/cm$^2$ to about $5.0\times10^5$ cells/cm$^2$ of growth surface, such as about $1.0\times10^5$ cells/cm$^2$ to about $4.5\times10^5$ cells/cm$^2$, such as about $1.5\times10^5$ cells/cm$^2$ to about $4.0\times10^5$ cells/cm$^2$, such as about $2.0\times10^5$ cells/cm$^2$ to about $3.5\times10^5$ cells/cm$^2$, or such as about $2.5\times10^5$ cells/cm$^2$ to about $3.0\times10^5$ cells/cm$^2$ of growth surface.

Oligodendrocyte Progenitor Cell Compositions

As discussed above, the present disclosure provides compositions comprising a population of oligodendrocyte progenitor cells (OPCs) as well as methods of making and using the same from use in the treatment of acute spinal cord injury and other related CNS conditions. In certain embodiments, the OPCs of the present disclosure are capable of producing and secreting one or more biological factors that may augment neural repair.

In one embodiment, a cell population can have a common genetic background. In an embodiment, a cell population may be derived from one host. In an embodiment, a cell population can be derived from a pluripotent stem cell line. In another embodiment, a cell population can be derived from an embryonic stem cell line. In an embodiment, a cell population can be derived from a hESC line. In an embodiment, a hESC line can be an H1, H7, H9, H13, or H14 cell line. In another embodiment, a cell population can be derived from an induced pluripotent stem cell (iPS) line. In an embodiment a cell population can be derived from a subject in need thereof (e.g., a cell population can be derived from a subject that is in need to treatment). In yet another embodiment, a hESC line can be derived from parthenotes, which are embryos stimulated to produce hESCs without fertilization.

In certain embodiments, the OPCs of the present disclosure express one or more markers chosen from Nestin, NG2, Olig1 and PDGF-Rα. In certain embodiments, the OPCs of the present disclosure express all of the markers Nestin, NG2, Olig1 and PDGF-Rα. In some embodiments, at least 70% of AST-OPC1 are positive for Nestin expression. In some embodiments, at least 30% of AST-OPC1 are positive for NG2 expression. In some embodiments, at least 70% of AST-OPC1 are positive for Olig1 expression. In some embodiments, at least 70% of AST-OPC1 are positive for PDGF-Rα expression. The specific markers and combinations of various markers expressed by the cell populations of the present disclosure can be determined and quantified, for example, by flow cytometry. Non-limiting examples of the markers expressed by the cells of the present disclosure are provided in FIG. 9.

In certain embodiments, the OPCs of the present disclosure are capable of secreting one or more biological factors.

In certain embodiments, the one or more biological factors secreted by the OPCs of the present disclosure may promote, without limitation, neural repair, axonal outgrowth and/or glial differentiation, or any combination thereof. In some embodiments, the OPCs are capable of secreting one or more factors that stimulate axonal outgrowth. In some embodiments, the OPCs are capable of secreting one or more factors promoting glial differentiation by neural precursor cells. In some embodiments, the OPCs are capable of secreting one or more chemoattractants for neural precursor cells. In some embodiments, the OPCs are capable of secreting one or more inhibitors of matrix metalloproteinases. In some embodiments, the OPCs are capable of secreting one or more factors inhibiting cell death after spinal cord injury. In some embodiments, the OPCs are capable of secreting one or more factors that are upregulated post-cellular injury and that aid in the clearance of misfolded proteins.

In certain embodiments, the OPCs are capable of producing and secreting one or more biological factors selected from MCP-1, Clusterin, ApoE, TIMP1 and TIMP2. In further embodiments the OPCs are capable of producing and secreting MCP-1 and one or more of the factors selected from Clusterin, ApoE, TIMP1 and TIMP2. In yet further embodiments, the OPCs are capable of producing and secreting all of the factors MCP-1, Clusterin, ApoE, TIMP1 and TIMP2.

In an embodiment, a biological factor can be secreted by a composition comprising a population of OPCs at a concentration of more than about 50 pg/ml, such as more than about 100 pg/ml, such as more than about 200 pg/ml, such as more than about 300 pg/ml, such as more than about 400 pg/ml, such as more than about 500 pg/ml, such as more than about 1,000 pg/ml, such as more than about 2,000 pg/ml, such as more than about 3,000 pg/ml, such as more than about 4,000 pg/ml, such as more than about 5,000 pg/ml, such as more than about 6,000 pg/ml, or such as more than about 7,000 pg/ml. In certain embodiments, a biological factor can be secreted by a composition comprising a population of cells comprising OPCs at a concentration ranging from about 50 pg/ml to about 100,000 pg/ml, such as about 100 pg/ml, such as about 150 pg/ml, such as about 200 pg/ml, such as about 250 pg/ml, such as about 300 pg/ml, such as about 350 pg/ml, such as about 400 pg/ml, such as about 450 pg/ml, such as about 500 pg/ml, such as about 550 pg/ml, such as about 600 pg/ml, such as about 650 pg/ml, such as about 700 pg/ml, such as about 750 pg/ml, such as about 800 pg/ml, such as about 850 pg/ml, such as about 900 pg/ml, such as about 1,000 pg/ml, such as about 1,500 pg/ml, such as about 2,000 pg/ml, such as about 2,500 pg/ml, such as about 3,000 pg/ml, such as about 3,500 pg/ml, such as about 4,000 pg/ml, such as about 4,500 pg/ml, such as about 5,000 pg/ml, such as about 5,500 pg/ml, such as about 6,000 pg/ml, such as about 6,500 pg/ml, such as about 7,000 pg/ml, such as about 7,500 pg/ml, such as about 8,000 pg/ml, such as about 8,500 pg/ml, such as about 9,000 pg/ml, such as about 10,000 pg/ml, such as about 15,000 pg/ml, such as about 20,000 pg/ml, such as about 25,000 pg/ml, such as about 30,000 pg/ml, such as about 35,000 pg/ml, such as about 40,000 pg/ml, such as about 45,000 pg/ml, such as about 50,000 pg/ml, such as about 55,000 pg/ml, such as about 60,000 pg/ml, such as about 65,000 pg/ml, such as about 70,000 pg/ml, such as about 75,000 pg/ml, such as about 80,000 pg/ml, such as about 85,000 pg/ml, such as about 90,000 pg/ml, such as about 95,000 pg/ml.

In certain embodiments, a biological factor can be secreted by a composition comprising a population of cells comprising OPCs at a concentration ranging from about 1,000 pg/ml to about 10,000 pg/ml, such as about 1,000 pg/ml to about 2,000 pg/ml, such as about 2,000 pg/ml to about 3,000 pg/ml, such as about 3,000 pg/ml to about 4,000 pg/ml, such as about 4,000 pg/ml to about 5,000 pg/ml, such as about 5,000 pg/ml to about 6,000 pg/ml, such as about 6,000 pg/ml to about 7,000 pg/ml, such as about 7,000 pg/ml to about 8,000 pg/ml, such as about 8,000 pg/ml to about 9,000 pg/ml, or such as about 9,000 pg/ml to about 10,000 pg/ml.

In certain embodiments, a biological factor can be secreted by a composition comprising a population of cells comprising OPCs at a concentration ranging from about 10,000 pg/ml to about 100,000 pg/ml, such as about 10,000 pg/ml to about 20,000 pg/ml, such as about 20,000 pg/ml to about 30,000 pg/ml, such as about 30,000 pg/ml to about 40,000 pg/ml, such as about 40,000 pg/ml to about 50,000 pg/ml, such as about 50,000 pg/ml to about 60,000 pg/ml, such as about 60,000 pg/ml to about 70,000 pg/ml, such as about 70,000 pg/ml to about 80,000 pg/ml, such as about 80,000 pg/ml to about 90,000 pg/ml, or such as about 90,000 pg/ml to about 100,000 pg/ml.

In some embodiments, Clusterin can be secreted by a composition comprising a population of cells comprising OPCs at a concentration ranging from about 1,000 pg/ml to about 100,000 pg/ml. In certain embodiments, Clusterin can be secreted by a composition comprising a population of cells comprising OPCs at a concentration ranging from about 10,000 pg/ml to about 50,000 pg/ml. In some embodiments, MCP-1 can be secreted by a composition comprising a population of cells comprising OPCs at a concentration ranging from about 500 pg/ml to about 50,000 pg/ml. In certain embodiments, MCP-1 can be secreted by a composition comprising a population of cells comprising OPCs at a concentration ranging from about 5,000 pg/ml to about 15,000 pg/ml. In some embodiments, ApoE can be secreted by a composition comprising a population of cells comprising OPCs at a concentration ranging from about 100 pg/ml to about 10,000 pg/ml. In certain embodiments, ApoE can be secreted by a composition comprising a population of cells comprising OPCs at a concentration ranging from about 500 pg/ml to about 5,000 pg/ml. In some embodiments, TIMP1 can be secreted by a composition comprising a population of cells comprising OPCs at a concentration ranging from about 100 pg/ml to about 10,000 pg/ml. In certain embodiments, TIMP1 can be secreted by a composition comprising a population of cells comprising OPCs at a concentration ranging from about 500 pg/ml to about 5,000 pg/ml. In some embodiments, TIMP2 can be secreted by a composition comprising a population of cells comprising OPCs at a concentration ranging from about 100 pg/ml to about 10,000 pg/ml. In certain embodiments, TIMP2 can be secreted by a composition comprising a population of cells comprising OPCs at a concentration ranging from about 500 pg/ml to about 5,000 pg/ml.

Pharmaceutical Compositions

The OPCs of the present disclosure can be administered to a subject in need of therapy per se. Alternatively, the cells of the present disclosure can be administered to the subject in need of therapy in a pharmaceutical composition mixed with a suitable carrier and/or using a delivery system.

As used herein, the term “pharmaceutical composition” refers to a preparation comprising a therapeutic agent or therapeutic agents in combination with other components, such as physiologically suitable carriers and excipients.

As used herein, the term "therapeutic agent" can refer to the cells of the present disclosure accountable for a biological effect in the subject. Depending on the embodiment of the disclosure, "therapeutic agent" can refer to the oligodendrocyte progenitor cells of the disclosure. Alternatively, "therapeutic agent" can refer to one or more factors secreted by the oligodendrocyte progenitor cells of the disclosure. Non-limiting examples of secreted factors are listed in FIG. 10.

As used herein, the terms "carrier", "pharmaceutically acceptable carrier" and "biologically acceptable carrier" may be used interchangeably and refer to a diluent or a carrier substance that does not cause significant adverse effects or irritation in the subject and does not abrogate the biological activity or effect of the therapeutic agent. In certain embodiments, a pharmaceutically acceptable carrier can comprise dimethyl sulfoxide (DMSO). In other embodiments, a pharmaceutically acceptable carrier does not comprise dimethyl sulfoxide. The term "excipient" refers to an inert substance added to a pharmaceutical composition to further facilitate administration of the therapeutic agent.

The therapeutic agent or agents of the present disclosure can be administered as a component of a hydrogel, such as those described in U.S. patent application Ser. No. 14/275,795, filed May 12, 2014, and U.S. Pat. Nos. 8,324,184 and 7,928,069.

The compositions in accordance with the present disclosure can be formulated for parenteral administration by injection, e.g., by bolus injection or continuous infusion. Formulations for injection can be presented in unit dosage form, e.g., in ampoules or in multi-dose containers, with an added preservative. The compositions can contain formulatory agents such as suspending, stabilizing and/or dispersing agents. In certain embodiments, the compositions can be formulated to be adapted for cryopreservation.

The compositions in accordance with the present disclosure can be formulated for administration via a direct injection to the spinal cord of a subject. In certain embodiments, a composition in accordance with the present disclosure can be formulated for intracerebral, intraventricular, intrathecal, intranasal, or intracisternal administration to a subject. In certain embodiments, a composition in accordance with the present disclosure can be formulated for administration via an injection directly into or immediately adjacent to an infarct cavity in the brain of a subject. In certain embodiments, a composition in accordance with the present disclosure can be formulated for administration through implantation. In certain embodiments, a composition in accordance with the present disclosure can be formulated as a solution.

In certain embodiments, a composition in accordance with the present disclosure can comprise from about $1\times10^6$ to about $5\times10^8$ cells per milliliter, such as about $1\times10^6$ cells per milliliter, such as about $2\times10^6$ cells per milliliter, such as about $3\times10^6$ cells per milliliter, such as about $4\times10^6$ cells per milliliter, such as about $5\times10^6$ cells per milliliter, such as about $6\times10^6$ cells per milliliter, such as about $7\times10^6$ cells per milliliter, such as about $8\times10^6$ cells per milliliter, such as about $9\times10^6$ cells per milliliter, such as about $1\times10^7$ cells per milliliter, such as about $2\times10^7$ cells per milliliter, such as about $3\times10^7$ cells per milliliter, such as about $4\times10^7$ cells per milliliter, such as about $5\times10^7$ cells per milliliter, such as about $6\times10^7$ cells per milliliter, such as about $7\times10^7$ cells per milliliter, such as about $8\times10^7$ cells per milliliter, such as about $9\times10^7$ cells per milliliter, such as about $1\times10^8$ cells per milliliter, such as about $2\times10^8$ cells per milliliter, such as about $3\times10^8$ cells per milliliter, such as about $4\times10^8$ cells per milliliter, or such as about $5\times10^8$ cells per milliliter. In certain embodiments, a composition in accordance with the present disclosure can comprise from about $1\times10^8$ to about $5\times10^8$ cells per milliliter, such as about $1\times10^8$ to about $4\times10^8$ cells per milliliter, such as about $2\times10^8$ to about $5\times10^8$ cells per milliliter, such as about $1\times10^8$ to about $3\times10^8$ cells per milliliter, such as about $2\times10^8$ to about $4\times10^8$ cells per milliliter, or such as about $3\times10^8$ to about $5\times10^8$ cells per milliliter. In yet another embodiment, a composition in accordance with the present disclosure can comprise from about $1\times10^7$ to about $1\times10^8$ cells per milliliter, such as about $2\times10^7$ to about $9\times10^7$ cells per milliliter, such as about $3\times10^7$ to about $8\times10^7$ cells per milliliter, such as about $4\times10^7$ to about $7\times10^7$ cells per milliliter, or such as about $5\times10^7$ to about $6\times10^7$ cells per milliliter. In an embodiment, a composition in accordance with the present disclosure can comprise from about $1\times10^6$ to about $1\times10^7$ cells per milliliter, such as about $2\times10^6$ to about $9\times10^6$ cells per milliliter, such as about $3\times10^6$ to about $8\times10^6$ cells per milliliter, such as about $4\times10^6$ to about $7\times10^6$ cells per milliliter, or such as about $5\times10^6$ to about $6\times10^6$ cells per milliliter. In yet another embodiment, a composition in accordance with the present disclosure can comprise at least about $1\times10^6$ cells per milliliter, such as at least about $2\times10^6$ cells per milliliter, such as at least about $3\times10^6$ cells per milliliter, such as at least about $4\times10^6$ cells per milliliter, such as at least about $5\times10^6$ cells per milliliter, such as at least about $6\times10^6$ cells per milliliter, such as at least about $7\times10^6$ cells per milliliter, such as at least about $8\times10^6$ cells per milliliter, such as at least about $9\times10^6$ cells per milliliter, such as at least about $1\times10^7$ cells per milliliter, such as at least about $2\times10^7$ cells per milliliter, such as at least about $3\times10^7$ cells per milliliter, such as at least about $4\times10^7$ cells per milliliter, or such as at least about $5\times10^7$ cells per milliliter. In an embodiment, a composition in accordance with the present disclosure can comprise up to about $1\times10^8$ cells or more, such as up to about $2\times10^8$ cells per milliliter or more, such as up to about $3\times10^8$ cells per milliliter or more, such as up to about $4\times10^8$ cells per milliliter or more, such as up to about $5\times10^8$ cells per milliliter or more, or such as up to about $6\times10^8$ cells per milliliter.

In an embodiment, a composition in accordance with the present disclosure can comprise from about $4\times10^7$ to about $2\times10^8$ cells per milliliter.

In yet another embodiment, a composition in accordance with the present disclosure can have a volume ranging from about 10 microliters to about 5 milliliters, such as about 20 microliters, such as about 30 microliters, such as about 40 microliters, such as about 50 microliters, such as about 60 microliters, such as about 70 microliters, such as about 80 microliters, such as about 90 microliters, such as about 100 microliters, such as about 200 microliters, such as about 300 microliters, such as about 400 microliters, such as about 500 microliters, such as about 600 microliters, such as about 700 microliters, such as about 800 microliters, such as about 900 microliters, such as about 1 milliliter, such as about 1 5 milliliters, such as about 2 milliliters, such as about 2.5 milliliters, such as about 3 milliliters, such as about 3.5 milliliters, such as about 4 milliliters, or such as about 4.5 milliliters. In an embodiment, a composition in accordance with the present disclosure can have a volume ranging from about 10 microliters to about 100 microliters, such as about 20 microliters to about 90 microliters, such as about 30 microliters to about 80 microliters, such as about 40 microliters to about 70 microliters, or such as about 50 microliters to about 60 microliters. In another embodiment, a composition in accordance with the present disclosure can have a volume ranging from about 100 microliters to about 1 milliliter, such as about 200 microliters to about 900 microliters, such as about 300 microliters to about 800 microliters, such as about 400 microliters to about 700 microliters, or such as about 500 microliters to about 600 microliters. In yet another embodiment, a composition in accordance with the present disclosure can have a volume ranging from about 1 milliliter to about 5 milliliters, such as about 2 milliliter to about 5 milliliters, such as about 1 milliliter to about 4 milliliters, such as about 1 milliliter to about 3 milliliters, such as about 2 milliliter to about 4 milliliters, or such as about 3 milliliter to about 5 milliliters. In an embodiment, a composition in accordance with the present disclosure can have a volume of about 20 microliters to about 500 microliters. In another embodiment, a composition in accordance with the present disclosure can have a volume of about 50 microliters to about 100 microliters. In yet another embodiment, a composition in accordance with the present disclosure can have a volume of about 50 microliters to about 200 microliters. In another embodiment, a composition in accordance with the present disclosure can have a volume of about 20 microliters to about 400 microliters.

In certain embodiments, the present disclosure provides a container comprising a composition comprising a population of OPCs derived in accordance with one or more methods of the present disclosure. In certain embodiments, a container can be configured for cryopreservation. In certain embodiments, a container can be configured for administration to a subject in need thereof. In certain embodiments, a container can be a prefilled syringe.

For general principles in medicinal formulation, the reader is referred to Allogeneic Stem Cell Transplantation, Lazarus and Laughlin Eds. Springer Science+Business Media LLC 2010; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. In certain embodiments, the composition can also comprise or be accompanied by one or more other ingredients that facilitate the engraftment or functional mobilization of the enriched target cells. Suitable ingredients can include matrix proteins that support or promote adhesion of the target cell type or that promote vascularization of the implanted tissue.

Uses of the Cells of the Present Disclosure

In various embodiments as described herein, the present disclosure provides methods of using a cell population that comprises pluripotent stem cell-derived OPCs for improving one or more neurological functions in a subject in need of therapy. In certain embodiments, methods for using pluripotent stem-cell derived OPCs in the treatment of acute spinal cord injury are provided. In other embodiments, methods for using pluripotent stem-cell derived OPCs in the treatment of other traumatic CNS injuries are provided. In other embodiments, methods for using pluripotent stem-cell derived OPCs in the treatment of non-traumatic CNS disorders or conditions are provided. In certain embodiments, a cell population in accordance with the present disclosure can be injected or implanted into a subject in need thereof.

In certain embodiments, methods for using pluripotent stem-cell derived OPCs in the treatment of conditions requiring myelin repair or remyelination are provided. The following are non-limiting examples of conditions, diseases and pathologies requiring myelin repair or remyelination: multiple sclerosis, the leukodystrophies, the Guillain-Barre Syndrome, the Charcot-Marie-Tooth neuropathy, Tay-Sachs disease, Niemann-Pick disease, Gaucher disease and Hurler syndrome. Other conditions that result in demyelination include but are not limited to inflammation, stroke, immune disorders, metabolic disorders and nutritional deficiencies (such as lack of vitamin B12). The OPCs of the present disclosure can also be used for myelin repair or remyelination in traumatic injuries resulting in loss of myelination, such as acute spinal cord injury.

The OPCs are administered in a manner that permits them to graft or migrate to the intended tissue site and reconstitute or regenerate the functionally deficient area. Administration of the cells can be achieved by any method known in the art. For example the cells can be administered surgically directly to the organ or tissue in need of a cellular transplant. Alternatively non-invasive procedures can be used to administer the cells to the subject. Non-limiting examples of non-invasive delivery methods include the use of syringes and/or catheters to deliver the cells into the organ or tissue in need of cellular therapy.

The subject receiving the OPCs of the present disclosure may be treated to reduce immune rejection of the transplanted cells. Methods contemplated include the administration of traditional immunosuppressive drugs such as, e.g., tacrolimus, cyclosporin A (Dunn et al., *Drugs* 61:1957, 2001), or inducing immunotolerance using a matched population of pluripotent stem cell-derived cells (WO 02/44343; U.S. Pat. No. 6,280,718; WO 03/050251). Alternatively a combination of anti-inflammatory (such as prednisone) and immunosuppressive drugs can be used. The OPCs of the invention can be supplied in the form of a pharmaceutical composition, comprising an isotonic excipient prepared under sufficiently sterile conditions for human administration.

Use in treatment of CNS traumatic injury. In certain embodiments, a cell population in accordance with the present disclosure can be capable of engrafting at a spinal cord injury site following implantation of a composition comprising the cell population into the spinal cord injury site.

In certain embodiments, a cell population in accordance with the present disclosure is capable of remaining within the spinal cord injury site of the subject for a period of about 180 days or longer following implantation of a dose of the composition into the spinal cord injury site. In other embodiments, a cell population in accordance with the present disclosure is capable of remaining within the spinal cord injury site of the subject for a period of about 2 years or longer following implantation of a dose of the composition into the spinal cord injury site. In further embodiments, a cell population in accordance with the present disclosure is capable of remaining within the spinal cord injury site of the subject for a period of about 3 years or longer following implantation of a dose of the composition into the spinal cord injury site. In yet further embodiments, a cell population in accordance with the present disclosure is capable of remaining within the spinal cord injury site of the subject for a period of about 4 years or longer following implantation of a dose of the composition into the spinal cord injury site.

In certain embodiments, a cell composition in accordance with the present disclosure is capable of reducing spinal cord injury-induced parenchymal cavitation in a subject. In certain embodiments, a lesion volume is reduced by formation of a tissue matrix in the spinal cord injury site. In certain embodiments, the cells of the present disclosure are capable of forming a tissue matrix in the spinal cord injury site within about 180 days or less. In certain embodiments, the subject with reduced injury-induced parenchymal cavitation is human.

In certain embodiments, a cell population in accordance with the present disclosure can be capable of reducing a volume of an injury-induced central nervous system parenchymal cavitation in about 12 months or less. In certain embodiments, a cell population in accordance with the present disclosure can be capable of reducing a volume of an injury-induced central nervous system parenchymal cavitation in a subject in about 6 months or less, about 5 months or less, or less than about 4 months. In certain embodiments, the subject is human.

In an embodiment, one or more cells from a cell population in accordance with the present disclosure can be capable of migrating from a first location to one or more second locations within the central nervous system of a subject in need thereof. In an embodiment, one or more cells from a cell population in accordance with the present disclosure can be capable of migrating from the spinal cord of a subject to an affected tissue within the brain of the subject. In one embodiment, one or more cells from a cell population in accordance with the present disclosure can be capable of migrating from a first location within the spinal cord of a subject to a second location at an affected tissue within the spinal cord of the subject. In one embodiment, one or more cells from a cell population in accordance with the present disclosure can be capable of migrating from a first location within the brain of a subject to a second location at an affected tissue within the brain of the subject. In one embodiment, one or more cells from a cell population in accordance with the present disclosure can be capable of migrating from a first location within the brain of a subject to an affected tissue within the spinal cord of the subject. In one embodiment, one or more cells from a cell population in accordance with the present disclosure can be capable of migrating from a first location within the spinal cord of a subject to a second location at an affected tissue within the spinal cord of the subject, as well as to one or more locations at one or more affected tissues within the brain of the subject. In one embodiment, one or more cells from a cell population in accordance with the present disclosure can be capable of migrating from a first location within the brain of a subject to a second location at an affected tissue within the brain of the subject, as well as to one or more locations at one or more affected tissues within the spinal cord of the subject.

In an embodiment, one or more cells from a cell population in accordance with the present disclosure can be capable of migrating from a first location to one or more second locations at one or more affected tissues within the central nervous system of a subject in less than about 150 days, such as less than about 100 days, such as less than about 50 days, or such as less than about 10 days. In an embodiment, one or more cells from a cell population in accordance with the present disclosure can be capable of migrating from a first location to one or more second locations at one or more affected tissues within the central nervous system of a subject in about 180 days or less.

Additional Embodiments

Additional embodiments of the present disclosure include the following:

1. A container containing a composition that comprises a population of allogeneic human oligodendrocyte progenitor cells (OPCs) that are capable of engrafting at a spinal cord injury site of a human subject following implantation of a dose of the composition into the spinal cord injury site.

2. The container according to 1, wherein the OPCs do not elicit a humoral or cellular immune response in the human subject within one year of administration when the subject undergoes a low dose immunosuppressant regimen that is discontinued at about 60 days after implantation of a dose of the composition into the spinal cord injury site.

3. The container according to either of the embodiments 1 or 2, wherein the OPCs are capable of remaining within the spinal cord injury site of said subject for a period of about 180 days or more following implantation of a dose of the composition into the spinal cord injury site.

4. The container according to any of the embodiments 1-3, wherein the OPCs are capable of remaining within the spinal cord injury site of said subject for a period of about 2 years or more following implantation of a dose of the composition into the spinal cord injury site.

5. The container according to any of the embodiments 1-4, wherein the OPCs are capable of forming a tissue matrix in the spinal cord injury site within about 180 days or less, thereby reducing spinal cord injury-induced parenchymal cavitation.

6. The container according to any of the embodiments 1-5, wherein the OPCs are capable of secreting MCP-1 and one or more factors selected from the group consisting of: Clusterin, ApoE, TIMP1 and TIMP2.

7. The container according to any of the embodiments 1-5, wherein the OPCs are capable of secreting all of the factors MCP-1, Clusterin, ApoE, TIMP1 and TIMP2.

8. The container according to any of the embodiments 1-7, wherein the dose of the composition comprises between about $2\times10^6$ and about $50\times10^6$AST-OPC1 cells.

9. The container according to 8, wherein the dose of the composition comprises between about $20\times10^6$ and about $50\times10^6$ AST-OPC1 cells.

The container according to 8, wherein the dose of the composition comprises between about $2\times10^6$ and about $20\times10^6$ AST-OPC1 cells.

10. A container containing a composition that comprises a population of allogeneic human oligodendrocyte progenitor cells (OPCs) that are capable of presenting at a spinal cord injury site of a subject and produce no detectable systemic toxicity in the subject following implantation of a dose of the composition into the spinal cord injury site.

11. The container according to 10, wherein the OPCs do not induce significant alterations in a hematology, coagulation, urinalysis or clinical chemistry parameter of the subject.

12. A method of reducing spinal cord injury-induced parenchymal cavitation in a human subject with an acute spinal cord injury, the method comprising administering to said subject a composition that comprises a population of allogeneic human oligodendrocyte progenitor cells (OPCs) that are capable of engrafting at a spinal cord injury site.

13. The method according to 12, wherein administering the composition comprises directly injecting the composition into the spinal cord injury site approximately 5 mm caudal of the spinal cord injury epicenter.

14. The method according to either of the embodiments 11-12, further comprising administering to the subject a low dose immunosuppressant regimen.

15. The method according to 14, wherein the immunosuppressant regimen comprises a tacrolimus dose of about 0.03 mg/kg/day per os, adjusted to maintain a trough blood concentration of about 3-7 ng/mL through about day 46 following the administering of the composition comprising a population of allogeneically derived OPCs, followed by tapering off and discontinuing the immunosuppressant regimen at about day 60 following the administering of the composition.

16. The method according to 12, wherein the OPCs are capable of remaining within the spinal cord injury site of said subject for a period of about 180 days or longer following the administration of the composition to the spinal cord injury site.

17. The method according to 12, wherein the OPCs are capable of remaining within the spinal cord injury site of said subject for a period of about 2 years or longer following the administration of the composition to the spinal cord injury site.

18. The method according to any of the embodiments 12-16, wherein the OPCs are capable of forming a tissue matrix in the spinal cord injury site of said subject within about 180 days or less, thereby reducing spinal cord injury-induced parenchymal cavitation.

19. The method according to any of the embodiments 12-17, wherein the subject has a thoracic or cervical spinal cord injury.

20. The method according to any of the embodiments 12-19, wherein the composition comprises between about $2\times10^6$ and about $50\times10^6$ AST-OPC1 cells.

21. A container containing a composition that comprises a population of oligodendrocyte progenitor cells (OPCs) that are capable of remaining within a spinal cord injury site of a subject at a concentration of greater than 1% of all cells present at the spinal cord injury site of said subject for a period of 180 days or more following implantation of a dose of the composition into the spinal cord injury site of the subject.

22. The container according to claim 9, wherein the percentage of OPCs that are present at the spinal cord injury site is measured be quantitative polymerase chain reaction (qPCR).

23. A container containing a composition comprising a population of oligodendrocyte progenitor cells (OPCs) that are capable of presenting at a spinal cord injury site of a subject and are capable of migrating less than 17 mm within a spinal cord of the subject as measured from a most rostral to a most caudal OPC over a period of about 180 days or more following implantation of a dose of the composition into the spinal cord injury site.

24. The container according to 23, wherein the OPCs are capable of migrating within a white matter tissue or a gray matter tissue of the spinal cord.

25. The container according to any one of the embodiments 21-24, wherein the composition comprises between about $2.0\times10^6$ and $50\times10^6$ AST-OPC1.

26. A container containing a composition that comprises a population of OPCs that are capable of presenting at a spinal cord injury site and are capable of producing no detectable increase in a frequency of allodynia in a subject following implantation of a dose of the composition into the spinal cord injury site.

27. The container according to 26, wherein the allodynia is measured in response to a normally non-noxious blunt force mechanical stimulus.

28. The container according to 26, wherein the allodynia is measured in response to a normally non-noxious cold temperature stimulus.

29. The container according to any one of the embodiments 26-28, wherein the allodynia is measured at two different anatomical sites on the subject.

30. The container according to any one of the embodiments 26-29, wherein the OPCs are capable of producing no detectable increase in the frequency of allodynia for a period of time ranging from 3 to 9 months post-implantation.

31. The container according to any one of the embodiments 26-30, wherein the composition comprises between about $2.0\times10^6$ and $50\times10^6$ AST-OPC1.

32. The container according to 31, wherein the composition comprises a pharmaceutically-acceptable carrier.

33. The container according to either of the embodiments 31 or 32, wherein the composition is formulated for administration via a direct injection into the spinal cord of a subject.

34. The container according to either of the embodiments 31 or 32 wherein the composition is formulated for intracerebral, intraventricular, intrathecal, intranasal or intracisternal administration to a subject 35. A method of inducing myelin repair or remyelination in a subject comprising administering a therapeutically effective amount of the composition according to any one of the previous claims to the subject.

36. The method according to 35, further comprising treating the subject to reduce immune rejection of the OPCs.

37. The method according to 36, further comprising administering an anti-inflammatory agent to the subject.

38. The method according to any one of the embodiments 35-37, wherein the subject has been diagnosed with a disease or pathology selected from the group consisting of: multiple sclerosis, leukodystrophy, Guillain-Barre Syndrome, Charcot-Marie-Tooth neuropathy, Tay-Sachs disease, Niemann-Pick disease, Gaucher disease, and Hurler Syndrome.

39. The method according to any one of the embodiments 35-37, wherein the subject has been diagnosed with a condition selected from the group consisting of: inflammation, stroke, immune disorders, metabolic disorders, and nutritional deficiencies.

40. The method according to any of the embodiments 35-37, wherein the subject has suffered a traumatic injury resulting in a loss of myelination.

41. The method according to 40, wherein the traumatic injury is an acute spinal cord injury.

42. The method according to 41, wherein the traumatic injury is cervical spinal cord injury.

43. The method according to 41, wherein the traumatic injury is thoracic spinal cord injury.

42. The method according to any of the embodiments 35-43, wherein the composition is surgically administered to the subject.

43. The method according to any of the embodiments 35-43, wherein the composition is administered to the subject using a non-invasive delivery method.

MATERIALS AND METHODS

The following paragraphs, describing the materials, systems and methods of several specific embodiments, are intended to be illustrative only and are not to be construed as limiting the scope of the present disclosure to the specific features or combinations of features described.

Animal Subjects. All procedures used were approved by a board-certified veterinarian and were conducted in accordance with the National Institute of Health Guide for the Care and Use of Laboratory Animals. Adult athymic nude rats (strain Crl:NIFI-Foxn1rnu-) were obtained from Charles Rivers Laboratories (Wilmington, Mass). $Rag2^{-/-}\gamma c^{-/-}$ mice and $shiverer^{-/-}$ mice were obtained from Jackson Laboratories (Bar Harbor, Me.) and bred in-house to generate Rag2$^{-/-}$γc$^{-/-}$/shi$^{-/-}$ homozygous mice. All animal subjects were housed in standard conditions with a 12 hr light/dark cycle, were provided food and water ad libitum, and were allowed to acclimate for a minimum of one week prior to surgery Differentiation of AST-OPC1 from hESCs. The WA01 (H1) hESC line was expanded in feeder-free conditions (Xu C, Inokuma M S, Denham J, Golds K, Kundu P, Gold J D, Carpenter M K. Feeder-free growth of undifferentiated human embryonic stem cells. *Nat Biotechnol.* 2001 Oct;19 (10):971-74; Li Y, Powell S, Brunette E, Lebkowski J, Mandalam R. Expansion of human embryonic stem cells in defined serum-free medium devoid of animal-derived products. *Biotechnol Bioeng.* 2005 Sep. 20;91(6):688-98). hESC colonies were lifted with collagenase and manual scraping and then seeded into ultra-low attachment flasks (Day 0) in 50% hESC growth media and 50% glial progenitor medium (GPM) containing 4 ng/mL of basic fibroblast growth factor (FGF) and 20 ng/mL epidermal growth factor (EGF) to stimulate embryoid body formation. On Day 1, media was replaced with 50% hESC growth media/50% GPM containing 20 ng/mL EGF and 10 μM all-trans-retinoic acid (RA). On Days 2-8, media was replaced daily with 100% GPM containing 20 ng/mL EGF and 10 μM RA. On Days 9-26, embryoid bodies were maintained in GPM/EGF media without RA, and media was replaced every 2 days. On Day 28, embryoid bodies were plated in Matrigel-coated flasks and cultured in GPM/EGF media for 7 days with media exchange every 2 days. On Day 34, cells were harvested with trypsin, replated in Matrigel-coated flasks, and cultured for an additional 7 days in GPM/EGF media, with media exchange every 2 days. On Day 41, cells were harvested with trypsin, filtered to remove residual cell aggregates, and cryopreserved in liquid nitrogen.

Analysis of differentiated AST-OPC1 by flow cytometry. Differentiated AST-OPC1 samples were assayed for the presence of surface and intracellular markers using standard flow cytometry. For surface marker staining, Day 41 AST-OPC1 samples were blocked with 10% heat-inactivated goat serum (HI FBS) and then incubated with primary antibody and/or isotype control (0.5 μg/5×10$^5$ cells, NG2, Invitrogen # 37-2300; Mouse IgG1 BD Biosciences # 55412) for 30 minutes at 2-8° C., washed, then and incubated with secondary antibody (goat-anti-mouse-IgG1-A488 Invitrogen A21121 at 0.25 μg/5×10$^5$ cells) for 30 minutes at 2-8° C. To exclude nonviable cells, propidium iodide (Sigma P4864 at 1 μg/mL) was added to the stained samples just prior to acquisition. All samples were then acquired and the data analyzed on the BD Biosciences FACSCalibur™ cytometer system using Cellquest Pro software.

For intracellular marker staining, Day 41 AST-OPC1 samples were tagged with ethidium monoazide (Sigma E2028 at 5 μg/mL) for dead cell discrimination followed by fixation using 2% Paraformaldehyde (PFA) and then permeabilization with cold 90% methanol. The cells were blocked with either 5% HI FBS (for October4) or 10% heat-inactivated goat serum (for Nestin) and then incubated with primary antibody and/or isotype control (goat anti-Oct4 Santa Cruz SC8629, normal goat IgG SC2028 at 0.15-0.5 μg/5×10$^5$ cells; Nestin Millipore MAB5326; MoIgG1 BD Biosciences 554121 at 0.5 μg/5×10$^5$ cells) for 30 minutes at 2-8° C., washed with stain buffer and incubated with secondary antibody (donkey-anti-goat-IgG-A488 Invitrogen A11055 or goat-anti-mouse-IgG1-A488 Invitrogen A21121 at 0.25 μg/5×10$^5$ cells) for 30 minutes at 2-8° C. All samples were then acquired and the data analyzed on the BD Biosciences FACSCalibur™ cytometer system using Cellquest Pro software.

Quantification of secreted factors in AST-OPC1 conditioned medium by Luminex. Conditioned media from 7 different AST-OPC1 lots was collected at the time of harvest (immediately prior to cryopreservation) and sent to Assay-Gate, Inc. (Ijamsville, Md.) for Luminex-based detection of 66 secreted factors. Secreted factors that were detected in all 7 lots and found to have putative roles in neural repair are reported.

In vitro neurite outgrowth assay. On Day 0, cortical tissue dissected from embryonic day 18 Sprague-Dawley rats was obtained from BrainBits, LLC (Springfield, Ill.) and dissociated to single cells according to the manufacturer's instructions. Dissociated cortical cells were seeded at 80,000 cells/0.5 mL/well into poly-L-lysine-coated 24 well plates and cultured in primary cortical neuron medium (PCN medium=Neurobasal Medium plus 0.5 mM L-glutamine, B-27 supplement, and penicillin/streptomycin, Life Technologies, Grand Island, N.Y.). On Day 4, each well received 0.5 mL additional PCN medium and a 0.4 μM pore transwell insert containing either 200,000 AST-OPC1 cells/0.3 mL PCN medium or 0.3 mL PCN medium alone. On Days 7 and 10, 50% of the medium in the bottom chamber of each well was exchanged.

Figures 2A, 2B, 2C, 2D, 2E:
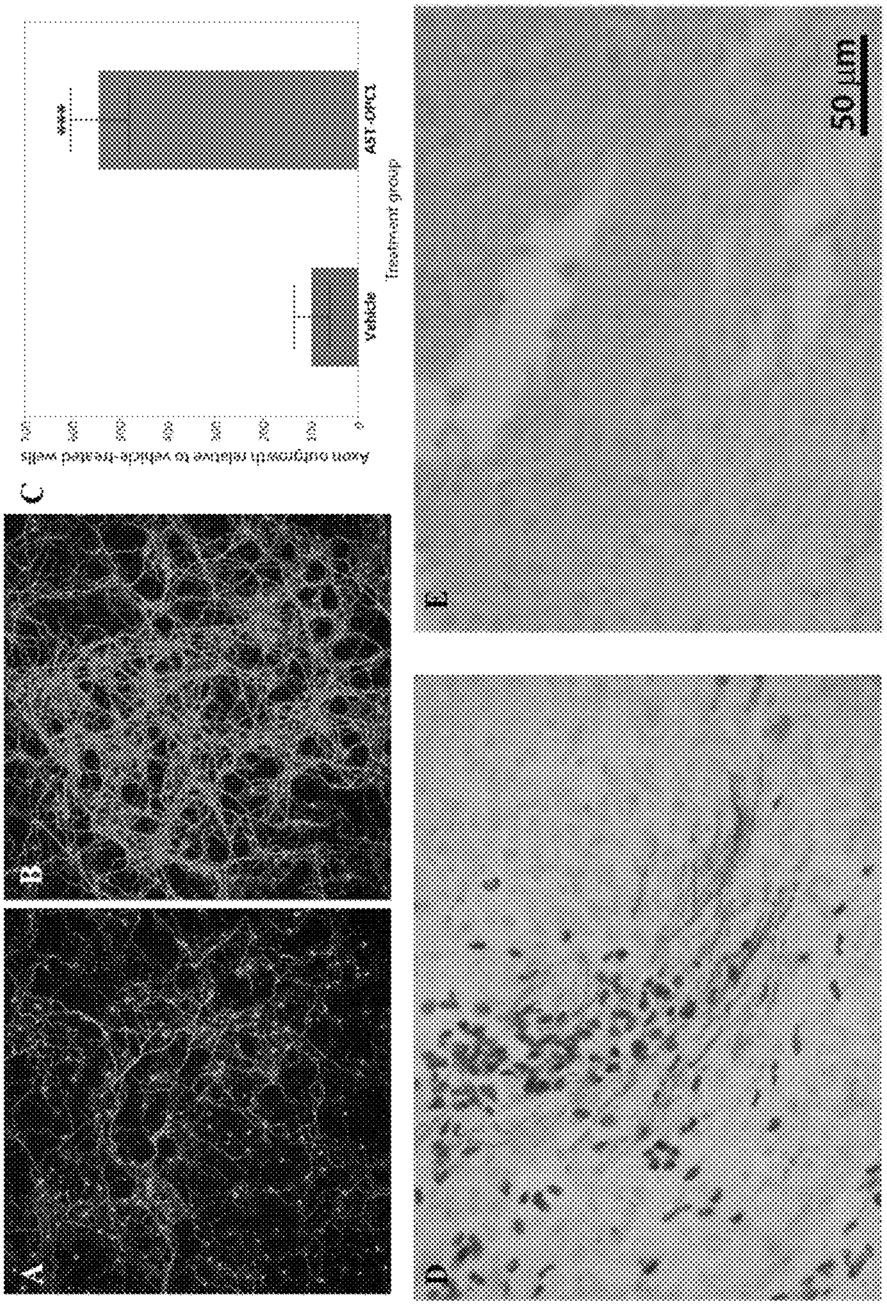
FIGS. 2A-2B show representative images of rat primary cortical neurons cultured in control medium for 14 days (FIG. 2A) or co-cultured with AST-OPC1 from day 4 to day 14 (FIG. 2B) and labeled by immunocytochemistry against the axonal marker SMI-312.
FIG. 2C depicts quantification of axon outgrowth in rat primary cortical neurons cultured with AST-OPC1 compared to vehicle control alone on day 14.
FIGS. 2D-2E show high magnification photomicrographs of thoracic spinal cord from immunodeficient $Rag2^{-/-}\gamma c^{-/-}/shi^{-/-}$ mice transplanted with AST-OPC1. By 2 months post-transplantation, myelinated fibers were detectable within the graft site in close association with cells positively labeled with the anti-human nuclei antibody (hNUC) (FIG. 2D), whereas no myelin staining was observed in the spinal cord outside the AST-OPC1 graft site (FIG. 2E).

On Day 14, transwell inserts and PCN medium were removed from each well, and primary cortical neurons were fixed with 4% paraformaldehyde/DPBS for 15 min at RT, followed by 3 washes in DPBS. Wells were incubated in blocking solution (10% normal goat serum/0.1% Triton X-100/DPBS) for 30 min at RT, followed by incubation with the anti-neurofilament antibody, SMI-312 (1:1000, Abcam ab24574) in blocking solution overnight at 4° C. Following 3 washes in DPBS, wells were incubated with a goat anti-mouse IgG-Alexa594 secondary antibody (1:400, Life Technologies A11032) and DAPI in blocking solution for 2 hr at RT. Following 3 washes in DPBS, plates were imaged on an INCell Analyzer 2000 (GE Healthcare, Pittsburg, Pa.), using a 10× objective to acquire 9 imaging fields per well. ImageJ software (NIH, Bethesda, Md.) was used to determine fluorescent area measurements of SMI-312 and DAPI positivity in each image. Because the SMI-312 antibody exhibited reactivity to cell axons and nuclei, the total area of DAPI positivity was subtracted from the total area of SMI positivity for each image, to determine the total area of axonal outgrowth. The average axonal outgrowth across the 9 imaging fields was then determined for each well and expressed as a percentage relative to the overall average axonal outgrowth of vehicle-treated wells for each culture plate. Results in FIG. 2C are the average of three independent experiments.

Thoracic spinal cord injury. Following at least one week of acclimation, athymic nude rats [Cr1:NIH-Foxn1$^{rnu}$] were subjected to a thoracic spinal cord crush/contusion injury at level T10. Rats were given an intraperitoneal (IP) injection of a 60 mg/kg ketamine/7.5 mg/kg xylazine cocktail to induce anesthesia, and then a midline skin incision was made at the T8 to T11 level of the thoracic spinal cord. The paravertebral muscles were dissected bilaterally to visualize the transverse apophyses. A laminectomy was performed at T10, and a midline contusion injury was induced using the Infinite Horizons Impactor (Precision Systems & Instrumentation, Fairfax, Va.) set to deliver a 200 kdyne force impact. Following contusion injury and wound closure, animals were given a subcutaneous (SC) injection of Lactated Ringer's Solution (LRS; 10 mL) and maintained on an isothermic pad until recovery from anesthesia. Following contusion injury, manual bladder expression was performed 2-3 times daily for each animal until voluntary bladder expression returned.

AST-OPC1 transplantation in injured nude rats and Shiverer/Rag2 mice. For athymic nude rats (Crl:NIH-Foxn1$^{rnu}$), AST-OPC1 was injected into the spinal cord 6-8 days post-contusion injury. Animals were positioned in a stereotaxic frame, and a 50 μL Hamilton syringe outfitted with a 32 gauge needle (1 inch long, 30° beveled tip) was used to deliver vehicle (Hank's Balanced Salt Solution, HBSS) or AST-OPC1 at $2.4\times10^6$ or $2.4\times10^5$ cells/rat into the dorsal spinal parenchyma adjacent to the contusion epicenter via four injections of 6 μL (high dose AST-OPC1 or HBSS) or a single 2.4 μL injection (low dose AST-OPC1).

The immunosuppressive article, anti-asialo GM1 antibody (GM1Ab, Wako 986-10001) was administered via an IP injection to all athymic nude rats two days prior to transplant surgery, on the day of transplantation, and two days after transplantation, and weekly thereafter as 1 mg/injection in 0.2 mL USP sterile saline for injection.

For Rag2$^{-/-}$γc$^{-/-}$/shi$^{-/-}$ (Shiverer), AST-OPC1 was injected into the uninjured spinal cord at T9-T10 at a dose ranging from $2.5\times10^5$ to $1\times10^6$ cells/mouse and at a concentration of $1\times10^5$ cells/μL using the same approach as described for athymic nude rats. No additional immunosuppressive agents were given to AST-OPC1-treated mice.

Animal perfusion and tissue processing for histology. Central and peripheral tissues were collected at autopsy and immersion fixed in 10% formalin for paraffin-embedding. For spinal cord, the approximate rostral and caudal extent of the affected spinal cord tissue, corresponding to approximately 1 cm rostral and 1 cm caudal to the contusion epicenter or site of administration, was dissected en bloc during necropsy. The tissue was processed for paraffin embedding using standard procedures. Spinal cord tissue was sectioned in the longitudinal/horizontal plane by microtome and 5 μm sections were obtained and mounted onto slides for subsequent hematoxylin and eosin (H&E) staining, ISH and IHC.

Whole body fixation was performed by transcardial perfusion with 0.9% saline followed by 4% PFA. For frozen tissue preparation, perfused tissue was post-fixed in 4% PFA overnight at 4° C. followed by cryoprotection in 30% sucrose/PBS for 72 hr at 4° C. Cryoprotected tissue was snap frozen on dry ice and stored at −80° C. until sectioning at 20 μm on a cryostat.

Myelin staining with Eriochrome cyanine. To identify myelinated fibers within the spinal cord, tissues were stained with Solochrome cyanine solution (Fisher Scientific, Pittsburg, Pa.) for 20 min at RT, rinsed briefly in tap water, and differentiated in 10% iron alum solution (Fisher Scientific, Pittsburg, Pa.) for 10 min at RT. Following a brief rinsing in tap water, slides were counterstained with Eosin-Y (Biocare Medical, Concord, Calif.), dehydrated through a sequential ethanol series, cleared with xylenes and coverslipped with EcoMount (Biocare Medical, Concord, Calif.). Stained slides were imaged with an Axiocam MRc5 camera mounted on an Observer D1 microscope (Carl Zeiss, Gottingen, Germany).

To visualize myelinated fibers, spinal cord tissue sections were washed briefly in $dH_2O$ and incubated for 30 minutes in a 0.2% acidic solution of Eriochrome (Solochrome) Cyanine RS (EC; Sigma, Cat. # E2502), followed by a 10 min differentiation in 5% iron alum, and several washes in $dH_2O$. Differentiation was completed with a 10 min incubation in borax-ferricyanide and washes in $dH_2O$. Sections were dehydrated in ascending ethanols, cleared in Histoclear™ and coverslipped with Permount™ (Fisher Scientific).

Characterization of transplanted AST-OPC1 by immunohistochemistry & in situ hybridization. All animals that received AST-OPC1 transplantation were assayed for the presence of human cells in the spinal cord. For paraffin-embedded tissue, in situ hybridization (ISH) was used to label nuclear human-specific Alu DNA repeat sequences, followed by colorimetric detection. Briefly, tissues were deparaffinized in xylenes and 100% ethanol and permeabilized using pepsin. Biotinylated Alu probes (Q151P.9900, Invitrogen, Carlsbad, Calif.) were hybridized to the tissue for 5 min at 95° C. followed by 2 hr at 37° C. Post-hybridization stringency washes were performed at 37° C. Slides were incubated with horseradish peroxidase (HRP) conjugate for 30 min at 37° C. Nickel-enhanced diaminobenzidene tetrahydrochloride (Ni-DAB, Vector Laboratories, Burlingame, Calif.) was used for HRP visualization. Slides were counterstained with nuclear Fast Red, dehydrated through a sequential ethanol series, defatted in xylenes and coverslipped with Permount™ (Fisher Scientific, Santa Clara, Calif.).

Immunohistochemistry was performed to identify human cells in fixed frozen tissue using human nuclei antiserum (MAB1281, Chemicon, 1:500) and to label cells in proliferating phases of the cell cycle (all phases except G0) in paraffin-embedded tissue using Ki67 antiserum (833-500, Abcam, Cambridge, Mass., 1:1000). If necessary, slides were deparaffinized using xylenes and 100% ethanol. Antigen retrieval pretreatment consisted of placing the slides in boiling citrate buffer (pH 6.0) and microwaving at full power for 10 min, followed by cooling to ambient temperature. Slides were rinsed in DPBS and incubated with blocking buffer (0.3% Triton X-100, 10% normal goat serum, 0.1% bovine serum albumin, 3% $H_2O_2$ in DPBS) for 1 hr at ambient temperature followed by incubation with primary antibody for 24 hr at 4° C. The sections were washed and incubated with biotinylated secondary antibody (BA-1000, Vector Laboratories, Burlingame, Calif., 1:500) for 1 hr at ambient temperature, washed and incubated with streptavidin-HRP (Vectastain Elite ABC kit, Vector Laboratories, Burlingame, Calif., 1:1000 in DPBS) for 1 hr at ambient temperature. Ni-DAB, (Vector Laboratories) was used for HRP visualization. Slides were counterstained with eosin, dehydrated through a sequential ethanol series, defatted in xylenes and coverslipped with Permount™ (Fisher Scientific, Santa Clara, Calif.).

Cavitation area measurements in the injured spinal cord. Measurements of cavity formation were performed on spinal cord tissues sectioned in the longitudinal (horizontal) plane and stained with Eriochrome cyanine/Eosin-Y as described above. Measurements were made on spinal cord sections from 10-12 subjects in each treatment group ($2.4\times10^5$ AST-OPC1, $2.4\times10^6$ AST-OPC1 or HBSS), using a single tissue section that contained the injury/graft epicenter for each animal. Area measurements were performed using ImageJ software (NIH, Bethesda, Md.) without knowledge of treatment group.

Biodistribution of transplanted AST-OPC1 by quantitative PCR. One week after thoracic spinal cord injury, rats were transplanted with two different doses of AST-OPC1 ($2.4\times10^5$ or $2.4\times10^6$ AST-OPC1) or HBSS vehicle control, using the methods described above. At 2, 14, and 180 days post-administration, blood, cerebral spinal fluid (CSF) and tissues were collected from the transplanted rats. These time points were chosen to reflect times before and after the expected restoration of the functional blood-spinal cord barrier, after which AST-OPC1 was unlikely to migrate out of the central nervous system.

One set of animals at each time point had samples harvested and processed for quantitative PCR (qPCR). At 2, 14 and 180 days after AST-OPC1 transplantation, animals were euthanized via $CO_2$ asphyxiation and subsequent exsanguinations and the following tissues were collected: spinal cord (cervical cord/brainstem, lumbar/thoracic cord), brain (cerebellum, forebrain), lungs, heart, liver, spleen, CSF, blood, meninges, kidney, small intestine and ovaries/testes. Tissues and CSF were flash frozen in isopentane chilled on dry ice and stored at −80° C. The presence of human DNA was assayed by amplifying a 232 base pair sequence of the human Alu Y repeat sequence using the ABI Prism 7700 Sequence Detection System. The mass of human genomic DNA detected in one microgram of rat genomic DNA extracted from each tissue was quantified using serial dilutions of human genomic DNA as standards. The lower limit of detection in the assay used was 100 fg human genomic DNA/μg rat genomic DNA. A positive signal for these sequences was interpreted as the presence of human cells in the tissue from which the DNA was extracted. All qPCR analyses were performed by Althea Technologies (San Diego, Calif.).

Also at 2, 14, and 180 days after AST-OPC1 transplantation, parallel sets of animals in each group were transcardially perfused with ice-cold 0.9% saline followed by ice-cold 4% paraformaldehyde in Sorensen's phosphate buffer. Spinal cords and brains were dissected and post fixed in 4% PFA overnight at 4° C. and cryoprotected with 30% sucrose in Dulbecco's phosphate buffered saline (DPBS) at 4° C. Tissue was embedded in Tissue-Tek O.C.T. compound (Ted Pella, Redding, Calif.) and frozen on dry ice. Spinal cords were sectioned longitudinally through the site of the cell or vehicle injections, extending approximately 2 cm in both rostral and caudal directions from the contusion epicenter. Brains were sectioned in the coronal plane at the levels of the olfactory bulbs, lateral ventricles, hippocampus and cerebellum. 20 μm cryosections were thaw-mounted onto SuperFrost Plus™ slides (Fisher Scientific, Fair Lawn, N.J.) and stored desiccated at −80° C. until use.

Clinical and toxicological assessments of AST-OPC1 -treated, contused rats. Toxicology studies of AST-OPC1-treated, contused male and female athymic nude rats were performed at MPI Research (Mattawan, Mich.) under GLP conditions. Observations for morbidity, mortality, injury, and the availability of food and water were conducted at least twice daily for all animals enrolled in toxicology studies. Clinical observations were conducted and body weights were measured and recorded twice weekly during the study. At study termination, necropsy examinations were performed, organ weights were recorded, blood and urine samples were collected for clinical pathology evaluations and selected tissues were examined microscopically by a board-certified veterinary pathologist who was blinded to animals' treatment groups.

Allodynia measurements on AST-OPC1-treated, contused rats. At approximately 3, 6, and 9 months post-transplantation, 10 male and 10 female rats were evaluated for allodynia or hypersensitivity in response to normally non-noxious mechanical (blunt probe) or cold (point application of acetone) stimuli, as described previously (Hulsebosch CE, Xu G, Perez-Polo J R, Westlund J R, Westlund K N, Taylor C P, McAdoo D J 2000 Rodent model of chronic pain after spinal cord contusion injury and effects of gabapentin. *J. Neurotrauma* 17(12):1205-1217). Baseline measurements were performed on uninjured non-transplanted rats (18 male/20 female). For each animal tested, stimuli were applied to the animal's dorsum for 3 trials at each point of a 9 point grid centered on the laminectomy site (27 mechanical stimuli and 27 cold stimuli per time point) and stimuli were applied to the glabrous surface of each paw for 5 trials of each stimulus (20 mechanical stimuli and 20 cold stimuli per time point). Each animal tested was observed for supraspinal responses to the stimuli according to the following parameters: three anatomical levels of assessment (at, above, and below the level of injury), two modalities (application of mechanical stimulation or cold stimulation), and two assay sites (dorsal skin surface of the trunk and glabrous tissue of the paws). The mechanical and cold hypersensitivity tests on the dorsal skin were separated by at least 2 hours for each animal. The dorsal skin tests were conducted on freely moving, non-anesthetized animals in a home cage or familiar environment. Testing on the glabrous tissue was conducted in a Plexiglas™ box test apparatus with wire mesh floor. Animals were habituated to the apparatus for 10 min prior to testing. With each modality, animals were randomly assigned to receive mechanical or cold stimuli first.

Mouse Tumorigenicity Studies of AST-OPC1 spiked with undifferentiated hESCs. Tumorigenicity studies were performed at MPI Research (Mattawan, Mich.) under GLP conditions. AST-OPC1 spiked with its parent hESC line, H1, was administered into the thoracic spinal cord of uninjured male and female CB-17/IcrCrl-Prkdcsci$^{scid}$Lyst$^{bg}$BR mice using the transplantation procedure described above. Animals were administered a total dose of $2\times10^6$ cells or HBSS as a single 0.01 mL injection and were monitored for up to 12 months for clinical signs of tumor formation: Cell-treatment groups and sample sizes were as follows: 100% H1, n=30; 50% H1, n=31; 10% H1, n=31; 5% H1, n=12; 1% H1, n=37; 100% AST-OPC1, n=129; HBSS, n=30. Microscopic examination of fixed hematoxylin and eosin (H&E) stained paraffin sections was performed on protocol-designated sections of tissues. The slides were examined by a board certified veterinary pathologist. A four-step grading system was utilized to define gradable lesions for comparison between treatment groups. Presence of human cells in observed tumors was confirmed by ISH as described above.

EXAMPLES

The following examples are not intended to limit the scope of what the inventors regard as their invention nor are they intended to represent that the experiments below are all or the only experiments performed.

Example 1

Derivation and Characterization of AST-OPC1

AST-OPC1 (formerly known as GRNOPC1) was generated by the differentiation of WA01 (H1) hESCs from a master cell bank (MCB) as described in the Materials and Methods. The differentiation process to produce AST-OPC1 requires 41 days and transitions the hESCs from undifferentiated cell colonies through embryoid bodies to become an adherent, dispersed cell population which is harvested and cryopreserved. Representative photomicrographs of the cells at different stages of the 41 day differentiation process are shown in FIG. 1A.

Figure 1B:
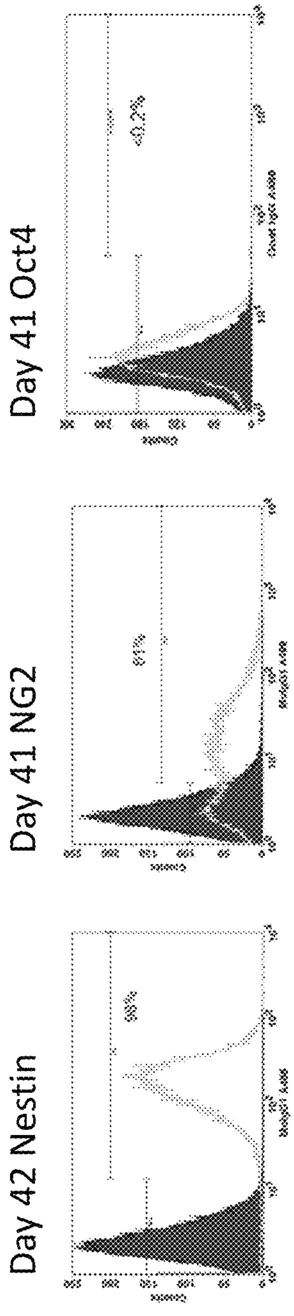
FIG. 1B shows representative flow cytometry data for the neural/glial lineage markers Nestin and NG2 and the pluripotency marker Oct4 from the day 41 AST-OPC1.

Analysis of 41 day differentiated AST-OPC1 by flow cytometry and immunocytochemistry (ICC) indicated that the cell population was comprised mostly of neural lineage cells of the early oligodendrocyte progenitor phenotype. By flow cytometry, over 90% of the cells were positive for Nestin and >50% were positive for NG2, a neural/glial proteoglycan expressed by oligodendrocyte progenitor cells (FIG. 1B). In addition, levels of the pluripotent stem cell marker, Oct4, were below the level of quantitation (<0.2%), indicating a lack of residual hESCs (FIG. 1B). Using an alternative high content image analysis assay, we further determined that the frequency of Oct4+ cells in AST-OPC1 was less than 0.05% (data not shown). Using the defined AST-OPC1 differentiation process, we produced over 75 lots of AST-OPC1, which we further characterized by ICC on day 41 for the presence of multiple markers of ectodermal, mesodermal, endodermal, and pluripotent cell types to assess the composition of the population and detect potential unwanted cells types (FIG. 9). In agreement with the flow cytometry results, ICC profiling indicated a cell population predominantly composed of early oligodendrocyte progenitor cells with few mature neuronal or astrocytic cells. The presence of endodermal, mesodermal or pluripotent cell types was undetectable to <1% of the differentiated AST-OPC1 cell population.

Example 2

Stimulation of Axonal Outgrowth In Vitro and Myelination In Vivo by AST-OPC1

A non-contact co-culture system using rat primary cortical neurons was used to assess the ability of AST-OPC1 to induce axonal outgrowth in vitro via paracrine signaling. Rat primary cortical neurons that were cultured 14 days in control medium (FIG. 2A) or with AST-OPC1 (FIG. 2B) and labeled by ICC with antibodies against the axonal marker SMI-312. Quantitative enumeration of the area of axonal outgrowth from 3 independent experiments demonstrated significantly greater axonal outgrowth with AST-OPC1 co-culture (FIG. 2C).

To assess the ability of AST-OPC1 to induce myelination of axons, cryopreserved AST-OPC1 cells were thawed and injected into the spinal cord of immunodeficient Rag2−/− γc−/−/shi−/− (Shiverer) mice that displayed a dysmyelinated phenotype due to their deficiency in myelin basic protein production. Two doses of AST-OPC1 ($2.5\times10^5$ or $1\times10^6$ cells) were injected into the uninjured spinal cord at thoracic level T9-T10. The mice were assessed two months post-implant for the presence of human cells and myelinated axons. Two months after implantation, human cells were detected by immunohistochemistry (IHC) using a human nuclear antigen antibody (hNUC, brown) in close association with myelinated fibers labeled with Eriochrome cyanine (EC, blue) within the thoracic spinal cord (FIG. 2D). No myelinated fibers or human cells were observed outside the vicinity of the graft site (FIG. 2E).

Figures 3A, 3B, 3C, 3D, 3E, 3F:
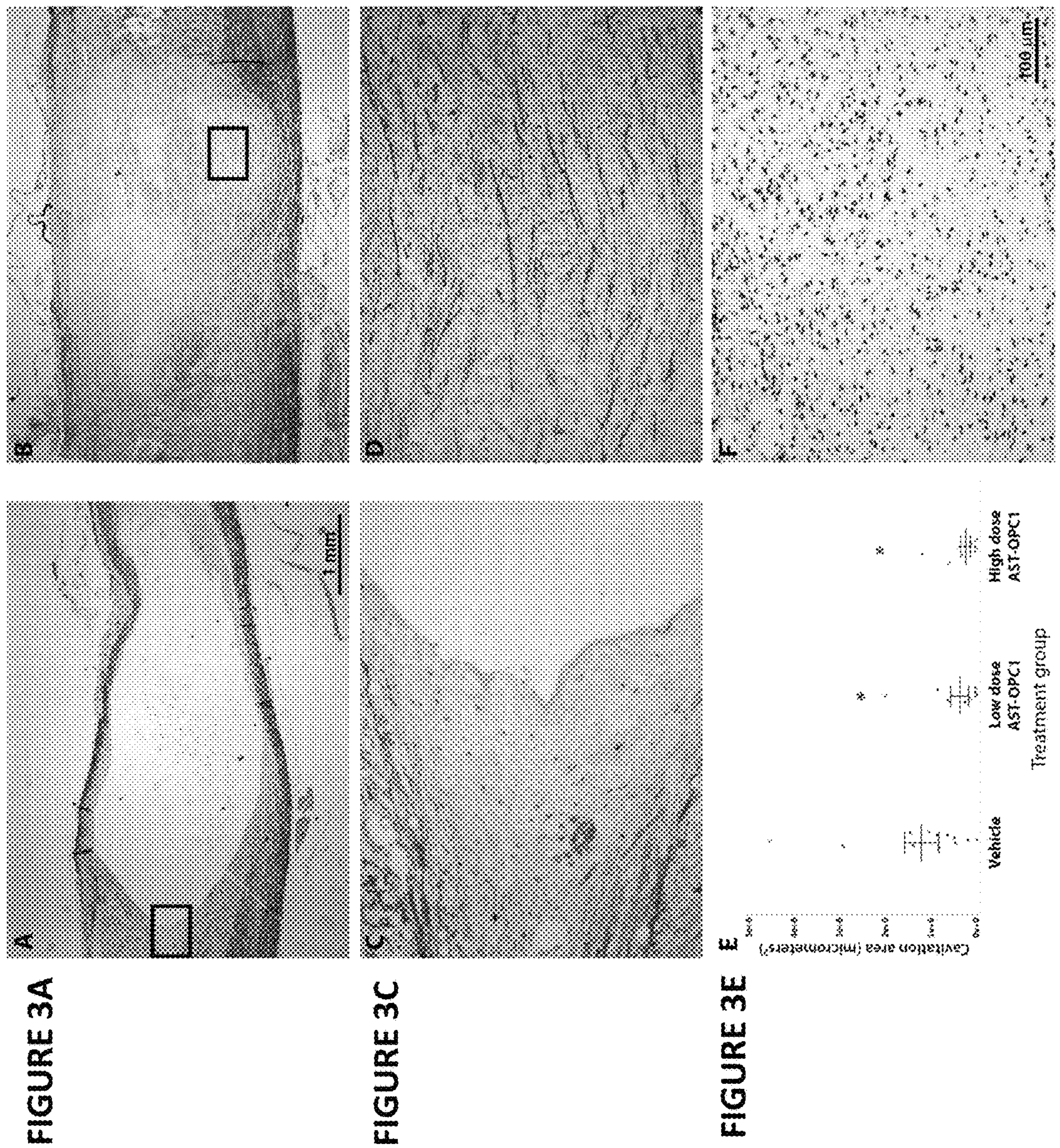
FIGS. 3A-3D depict representative low and high magnification photomicrographs of the injury/graft site in a rat model of contusion injury 9 months after thoracic spinal cord injury and injection of vehicle (FIG. 3A and FIG. 3C) or transplantation of AST-OPC1 (FIG. 3B and FIG. 3D). At 9 months post-contusion, vehicle-treated animals exhibited redirection of myelinated fibers around the lesion cavity (FIG. 3C), whereas cavitation was reduced in AST-OPC1-treated animals, and myelinated fibers were visible within the injury/graft site (FIG. 3D).
FIG. 3E shows dot plot of cavitation area 9 months after thoracic spinal cord injury and vehicle or AST-OPC1 treatment. Asterisk denotes significance relative to vehicle treatment based on two-tailed Student's t-test ($p<0.05$). Horizontal lines denote mean plus standard error of the mean (SEM) for each treatment group (vehicle mean cavitation area±SEM=1.29±0.372 mm2, n=12; low-dose AST-OPC1 mean cavitation area±SEM=0.378±0.201 mm2, n=10, p=0.033; high-dose AST-OPC1 mean cavitation area±SEM=0.244±0.111 mm2 n=11, p=0.0125).
FIG. 3F shows representative photomicrograph of an adjacent tissue section from the AST-OPC1-treated animal in FIGS. 3B and 3D, showing positive labeling with a human Alu DNA repeat sequence probe by in situ hybridization (brown nuclear signal, eosin counterstain) within the same region exhibiting myelinated fibers.

AST-OPC1 survived in the lesion site of rats with spinal cord injuries and preserved myelinated fibers and reduced cavity formation after thoracic spinal cord injury. In a collection of studies, athymic nude rats [Crl:NIH-Foxn1rnu] received a 200 kdyne contusion injury at T10 using the Infinite Horizons Impactor (Precision Systems & Instrumentation, Fairfax, Va.) and were implanted with $2.4\times10^5$ or $2.4\times10^6$ AST-OPC1 or HBSS vehicle control at 6-9 days post-injury as described in the Materials and Methods. Nine months post-implantation, the lesion sites were examined histologically. In control injured rats injected with vehicle, extensive parenchymal cavitation was observed (FIGS. 3A and 3C). The cavity was often large, extending rostrocaudally across multiple spinal cord segments from the epicenter of the injury site. Little to no cellularity existed in the cavity. Myelinated axons approached the injury cavity and halted their progression as evidenced by the presence of dystrophic endbulbs, or changed path to circumvent the contusion cavity. By contrast, injured animals injected with AST-OPC1 showed much less cavitation (FIGS. 3B and 3D). In sections from the AST-OPC1 transplanted animals, myelinated axons stained with EC could be seen to enter and traverse the injury site. Similar results were observed in 7 individual studies where AST-OPC1 was injected into nude rats with thoracic contusion injuries. In the largest study, parenchymal cavitation was quantified for a subset of animals by a histologist who was blinded to the animals' treatment group. In control animals injected with HBSS vehicle, measurable cavitation at the injury site was common and observed in 11 out of 12 (92%) animals, which typically exhibited large cavities ranging from 120-4520 $mm^2$ (FIG. 3E). By contrast, rats injected with AST-OPC1, regardless of dose, showed reduced parenchymal cavitation with 12 out of 21 animals showing no injury-related cavities (low dose AST-OPC1 animals with cavitation, range=120-1985 mm2; high dose AST-OPC1 animals with cavitation, range=20-1185 $mm^2$, FIG. 3E). A statistically significant reduction in mean cavitation area was observed with the high dose of AST-OPC1 (p=0.0325), while a similar, non-significant trend was observed with the low dose of AST-OPC1 (p=0.0814). Within the lesion site of AST-OPC1 treated animals, positive labeling with a human-specific Alu DNA repeat sequence probe (hAlu) using in situ hybridization (ISH) confirmed that human cells were resident in the lesion site in the area of the myelinated fibers at 9 months post-implant (FIG. 3F).

Example 3

Identification and Quantification of Factors Secreted by AST-OPC1

To identify candidate paracrine factors mediating AST-OPC1 biological activity, including stimulation of axonal outgrowth in vitro and myelination in vivo, conditioned media from 7 different AST-OPC1 lots was collected at the time of harvest (immediately prior to crypreservation) and sent to Assaygate, Inc. (Ijamsville, Md.), for Luminex® assay for detection and quantification of 66 secreted factors [AST-OPC1-conditioned medium contained multiple proteins with putative roles in neural repair. Consistent with previous findings (Zhang Y W, Denham J, Thies R S. Oligodendrocyte progenitor cells derived from human embryonic stem cells express neurotrophic factors. *Stem Cells Dev.* 2006 December;15(6):943-52), all 7 tested AST-OPC1 lots secreted MCP-1, a factor thought to act as a chemoattractant for neural precursor cells (Tang S K, Knobloch R A, Maucksch C, Connor B. Redirection of doublecortin-positive cell migration by over-expression of the chemokines MCP-1, MIP-1α and GRO-α in the adult rat brain. *Neuroscience.* 2014 February: 240-248) and promoting glial differentiation of neural precursor cells (Gordon R J, Mehrabi N F, Maucksch C, Connor B. Chemokines influence the migration and fate of neural precursor cells from the young adult and middle-aged rat subventricular zone. *Exp Neurol.* 2012 January;233(1):587-94). It was discovered that all 7 tested lots further secreted the following factors: Clusterin, ApoE, TIMP1 and TIMP2 (FIG. 10).

TABLE 1

Quantification of secreted factor production in individual AST-OPC1 lots.

| Secreted Factor (pg/mL) | OPC1 Lot A | OPC1 Lot B | OPC1 Lot C | OPC1 Lot D | OPC1 Lot E | OPC1 Lot F | OPC1 Lot G |
|---|---|---|---|---|---|---|---|
| Clusterin | 44,639 | 45,924 | 11,255 | 20,563 | 13,355 | 13,716 | 59,170 |
| MCP1 | 10,118 | 10,086 | 10,048 | 10,040 | 10,039 | 10,136 | 10,037 |
| APOE | 2,558 | 3,637 | 1,330 | 2,694 | 968 | 2,995 | 3,904 |
| TIMP1 | 2,580 | 4,149 | 1,863 | 1,263 | 1,064 | 2,778 | 6,150 |
| TIMP2 | 2,064 | 2,165 | 916 | 1,008 | 733 | 1,084 | 2,064 |

Conditioned medium sampling was performed on the final day of AST-OPC1 production, prior to cell cryopreservation. Conditioned medium was assayed for the presence of 66 secreted factors using a standard Luminex® platform. Concentrations are shown as the mean and standard deviation of the 7 assayed lots. Abbreviations: ApoE, apolipoprotein E; MCP-1, monocyte chemoattractant protein 1; TIMP1 & TIMP2, tissue inhibitor of metalloproteinases 1 and 2. Further details on the collection of AST-OPC1 conditioned medium and secreted factor detection by Luminex® are reported in Priest C A, Manley N C, Denham J, Wirth E D 3rd, Lebkowski J S, Preclinical safety of human embryonic stem cell-derived oligodendrocyte progenitors supporting clinical trials in spinal cord injury, *Regen Med.* 2015 November;10(8):939-58.

Example 4

Biodistribution of AST-OPC1

We conducted a biodistribution study to examine the potential of AST-OPC1 to migrate within the spinal cord and distribute to tissues outside the spinal cord following direct administration into the injured thoracic spinal cord. One of two doses of cryopreserved AST-OPC1 ($2.4\times10^5$ or $2.4\times10^6$) was administered into athymic nude rats 6-9 days after a 200 kdyne T9-10 spinal cord contusion injury and animals were maintained for 2, 14 and 180 days to examine biodistribution of the cells. These time points were chosen to reflect times before and after the expected restoration of the functional blood-spinal cord barrier, after which AST-OPC1 was unlikely to migrate out of the central nervous system. Ten females were included at each of the three time points for each of the three treatment groups (HBSS vehicle control, $2.4\times10^5$ AST-OPC1 or $2.4\times10^6$ AST-OPC1). For the 180 day time point, an additional group of 10 males was included which received the high dose of AST-OPC1. At 2, 14 and 180 days post-administration, 5 animals from each time point and treatment group were euthanized and had central nervous system and peripheral tissues collected including spinal cord (cervical cord/brainstem, lumbar/thoracic cord), brain (cerebellum, forebrain), blood, gonads, liver, heart, lung, kidney, spleen and small intestine. Samples were homogenized and assayed for the presence of human cells based on detection of hAlu DNA by quantitative polymerase chain reaction (qPCR). The lower limits of quantitation and detection for hAlu by qPCR in this assay was 1 pg human genomic DNA/μg rat DNA and 100 fg human genomic DNA/μg rat DNA, respectively.

At all time points assayed, hAlu was detected at less than the limit of quantification (<1 pg human gDNA/μg nude rat gDNA) in all rat peripheral tissues sampled, including blood, gonads, liver, heart, lung, kidney, spleen, and small intestine. Of the 280 peripheral tissue samples analyzed for hAlu by qPCR, only 9 (3.2%) showed detectable but non-quantifiable levels of human DNA. This frequency was close to the incidence of false positive samples (2 of 120 or 1.7%) observed in tissues from animals injected with HBSS. These data thus suggested that, if present, human cells were very rare in peripheral tissues.

Figure 4A:
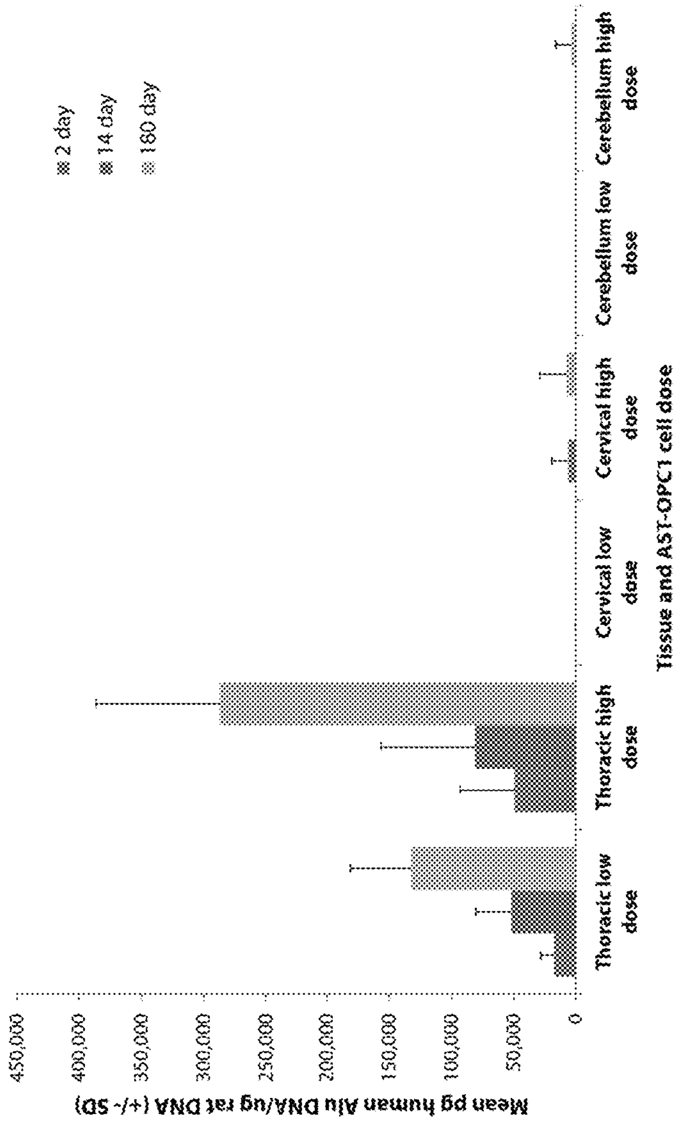
FIG. 4A depicts quantification of human cell survival in the central nervous system in AST-OPC1 treated, spinal cord injured rats.

At all time points, AST-OPC1 was found in the CNS, especially at the lesion site of the thoracic spinal cord (FIG. 4A). In most cases, hAlu was detected in the thoracic spinal cord at >10,000 pg human DNA per μg rat DNA (>1.0% human cells). The amount of human DNA in the thoracic spinal cord increased between 2 days and 180 days, although the difference in human DNA in the thoracic spinal cord did not appear to increase linearly with the dose of AST-OPC1.

In the cervical spinal cord, most animals had much reduced but measurable hAlu levels (≥1-10,000 pg human DNA/μg nude rat DNA). Only two animals (1 at the 180 day time point and 1 at the 2 day time point) that received $2.4\times10^6$ AST-OPC1 had high levels of hAlu in this region (≥10,000 pg human DNA/μg nude rat DNA).

Only 1 rat in the 180 day termination group receiving $2.4\times10^6$ AST-OPC1 had high levels of hAlu (≥10,000 pg human gDNA/ug nude rat gDNA) in the cerebellum. However, this data point may reflect a spurious result, as very few human cells were detected in the animal's adjacent cervical spinal cord, a site more proximal to the injection site. An additional 3 animals in the 180 day termination group had low levels of hAlu in the cerebellum (≥1-100 pg human DNA/μg nude rat DNA).

Figure 4B:
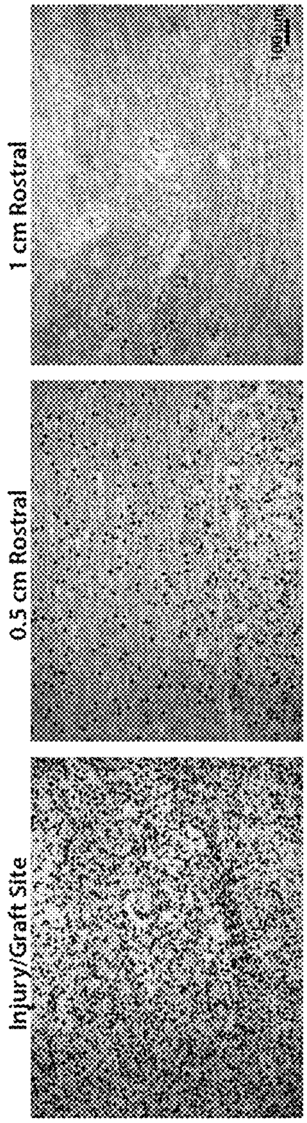
FIG. 4B shows histological assessment of the presence of human cells at and rostral to the injury site at 180 days post-administration as determined by immunohistochemistry using antibodies against human nuclear antigen (hNUC). Magnification=100×.

These PCR-based biodistribution results were confirmed by histological analysis of serial tissue sections of the thoracic spinal cord extending from caudal of the injury site, through the injury site, and rostral to the cerebellum from the remaining 5 animals per treatment group at each time point. The greatest concentration of human cells as identified by IHC for hNUC was at the injection site in area of the injury (FIG. 4B). The concentration of parenchymal AST-OPC1 diminished with distance from the injury epicenter. AxioVision image analysis software (AxioVS 40 V 4.6.3.0, Carl Zeiss Imaging Solutions) was used to measure the maximum rostrocaudal length of spinal cord between hNUC positive cells. The rostrocaudal extent of AST-OPC1 intraparenchymal distribution increased with time post-transplant, with distances of 15-17 mm observed between the most rostral and caudal migrating cells at the 180 day time point. AST-OPC1 migrated within the gray and white matter of the parenchyma and did not appear isolated by glial scarring or other anatomical barriers. Further analysis showed that, while greater numbers of AST-OPC1 migrated away from the injury epicenter in the animals that received the high dose of cells, the extent of migration was independent of the cell dose administered in this study.

Example 5

Toxicology Assessment of AST-OPC1

Three toxicology studies were conducted in accordance with Good Laboratory Practices (GLP) which investigated the potential toxicity of AST-OPC1 for the treatment of spinal cord injury. These studies specifically addressed potential toxicity issues of AST-OPC1 related to its 1) delivery to the spinal cord, 2) impact on organ function, 3) induction of allodynia, and 4) tumorigenicity. For the toxicology studies, a rat spinal cord contusion injury was utilized to mimic as closely as possible the conditions that will be encountered with patients with non-lacerating spinal cord crush injuries. In each study, rats were given a moderate 200 kdyne contusion injury and transplanted with either cryopreserved AST-OPC1 or HBSS vehicle. For transplantation, cryopreserved, thawed and prepared AST-OPC1 was injected approximately 6-9 days post-injury into the lesion site of these animals using the cell delivery methodology intended for use in the proposed clinical trial. The three toxicology studies examined contused male and female rats, of which 299 and 285 were injected with vehicle and AST-OPC1, respectively. AST-OPC1 doses of $2.4\times10^5$ and $2.4\times10^6$ cells were assessed.

Vehicle and AST-OPC1 transplanted rats were examined at 2, 6, 9 and 12 months post-injury for any negative impact on systemic organ function as measured by testing blood and urine analytes. FIG. 11 describes the metabolic and hematologic parameters examined to assess the potential systemic toxicity of AST-OPC1. The collective data from these studies suggested that AST-OPC1 did not induce any significant alterations in hematology, coagulation, urinalysis or clinical chemistry parameters compared to injured vehicle control animals. Some elevation in individual parameters, especially in liver enzymes and urea nitrogen were observed occasionally in animals receiving either AST-OPC1 or vehicle, likely due to the spinal cord injury itself or to the prolonged use of immunosuppression. There were no statistically significant differences in the mortality, body weights or clinical observations including behavioral activity, excretion, external appearance, or skin condition between the AST-OPC1 and vehicle treated contused rats. A common cause of death in all groups was septicemia/inflammation, not related to AST-OPC1 but likely a reflection of the immunocompromised state of the animals and their spinal cord injury. Many deaths were also related to urogenital dysfunction, inflammation, obstruction and/or calculi. The occurrence or frequency of these urogenital events was not considered related to AST-OPC1, as they were observed with similar frequency across all groups.

Many individuals with spinal cord injuries report musculoskeletal, neuropathic and visceral pain (Siddall P J, Taylor D A, McClelland J M, Rutkowski S B, Cousins M J. Pain report and the relationship of pain to physical factors in the first 6 months following spinal cord injury. *Pain.* 1999 May;81(1-2):187-97; Siddall P J, McClelland J M, Rutkowski S B, Cousins M J. A longitudinal study of the prevalence and characteristics of pain in the first 5 years following spinal cord injury. *Pain.* 2003 June;103(3):249-57). To investigate this, all animals that received spinal cord injuries were monitored for autophagia, and other general behavioral indicators of pain. Across the three toxicology studies, only 7 of 584 injured rats (3 vehicle and 4 AST-OPC1) showed signs of autophagia.

Figure 5:
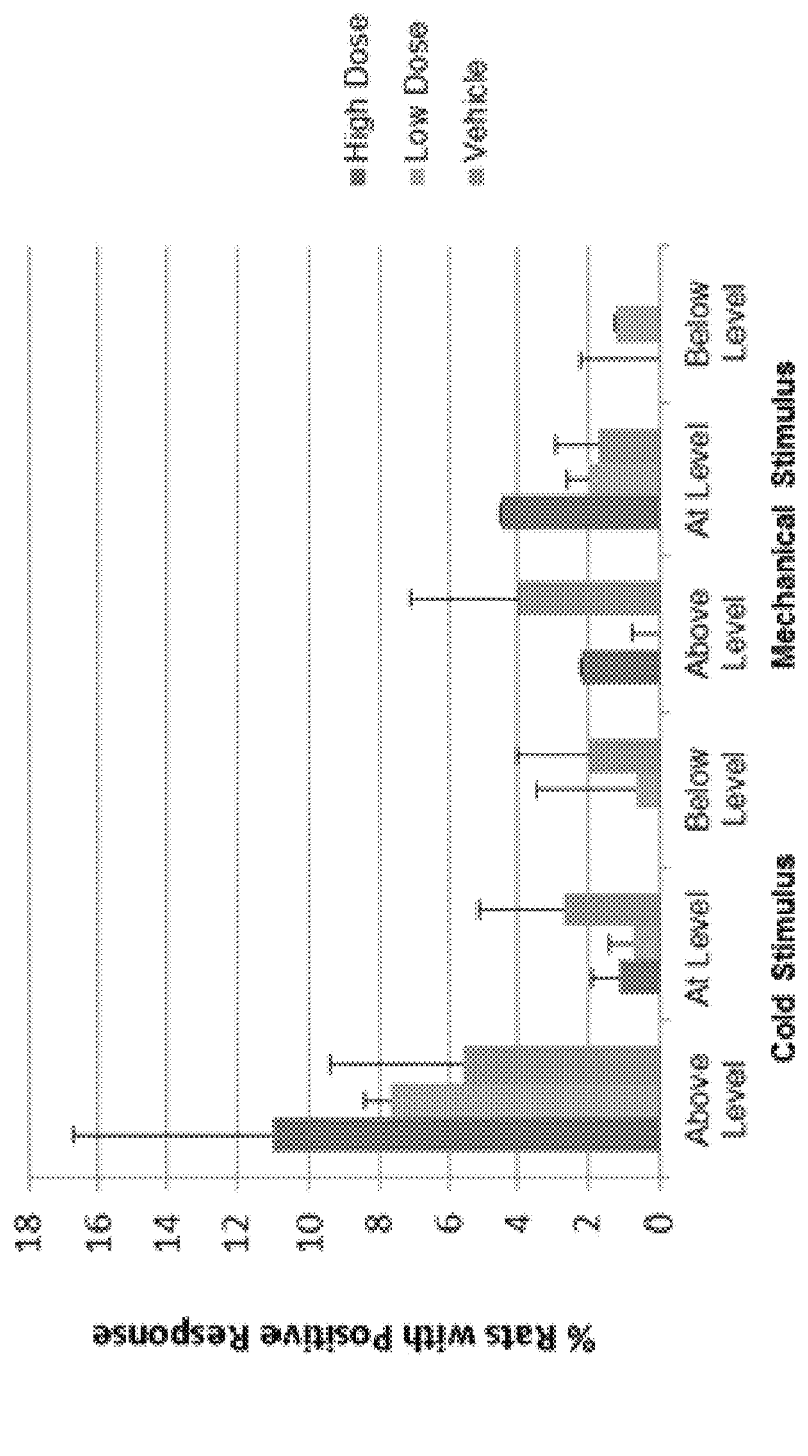
FIG. 5 depicts measurement of allodynia in spinal cord injured rats 9 months after administration of AST-OPC1.

Additional behavioral tests were performed to assess if AST-OPC1 impacted the frequency of allodynia in rats with spinal cord injuries. At approximately 3, 6, and 9 months post transplantation, animals in the largest toxicology study were evaluated for allodynia, hypersensitivity in response to normally non-noxious mechanical (blunt probe) or cold (point application of acetone) stimuli. To assure that the mechanical probe and cold (acetone) stimuli were non-aversive, the methods were initially used on the dorsal skin surface of 18 random male and 20 random female healthy rats from the study prior to laminectomy to establish baseline responses. Each animal tested was observed for supraspinal responses to the stimuli according to the following parameters: three anatomical levels of assessment (at, above, and below the level of injury), two modalities (application of mechanical stimulation or cold stimulation), and two assay sites (dorsal skin surface of the trunk and glabrous tissue of the paws). At 9 months post-administration, animals treated with AST-OPC1 did not show significant changes in their response profile, relative to vehicle controls, for either modality or at any anatomical sites, and did not display signs of allodynia (FIG. 5). Data are expressed as percent positive responses.

Example 6

Tumorigenicity Assessment of AST-OPC1

Macroscopic and microscopic examinations were performed by an independent veterinary pathologist who was blinded to the animals' treatment groups to ascertain whether AST-OPC1 administration resulted in any particular pathology either within or outside the central nervous system. Such analysis also included assessments for teratoma or ectopic tissue formation. For this analysis, teratomas were defined as expansile proliferations or masses which appeared to have arisen from at least 2 different embryonic germ layers (endodermal, mesodermal and/or ectodermal). Ectopic tissue was defined as tissue not normally occurring in the tissue or organ examined. For these analyses over 50 tissues were examined from each animal including the longitudinal extent of the spinal cord and 5 levels of the brain. There were no macroscopic or microscopic pathologic findings outside the spinal cord that were associated with AST-OPC1 in either male or female rats from the 2, 6, or 9 month termination groups.

The entire length of the thoracic and cervical spinal cords and 5 levels of the brain (medulla/pons, cerebellum, midbrain, forebrain and olfactory bulbs) were examined for teratomas and ectopic tissue. Teratomas were not observed in the spinal cord or brain in any of the 252 animals examined 2, 6, or 9 months post-administration. In agreement with this, cells within the injury/graft site exhibited very low positivity for the proliferation marker, Ki67, at 9 months post administration. Further, ISH labelling with an hAlu probe indicated robust graft survival in the thoracic spinal cord of 239 out of the 252 assessed animals examined 2, 6, or 9 months post-administration.

Figures 6A, 6B, 6C, 6D, 6E:
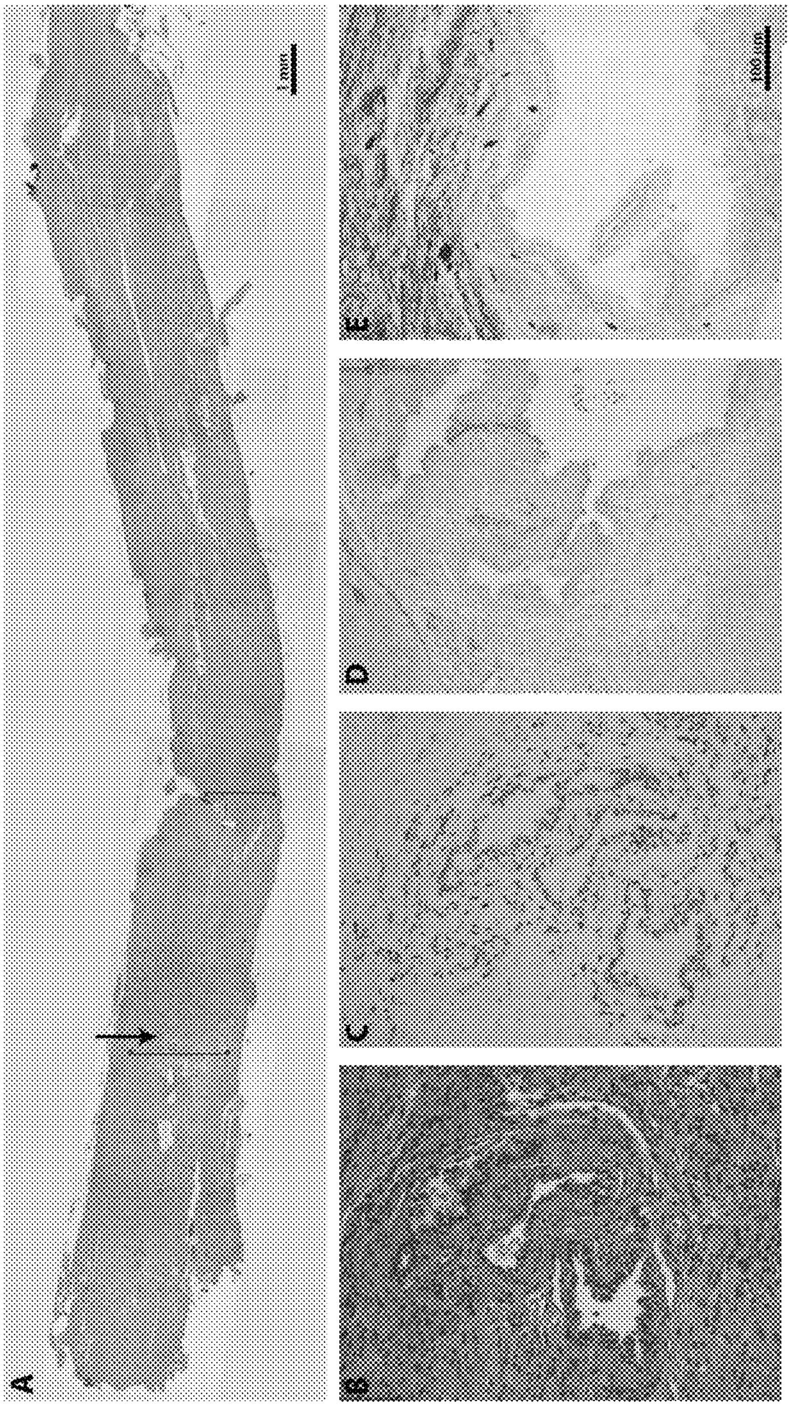
FIGS. 6A-6E depict cystic-like epithelial structures in within the AST-OPC1 graft site 6 months after administration, observed on 6 of the 252 animals injected with AST-OPC1. In a photographic montage of the contused spinal cord (FIG. 6A), brackets indicate the approximate boundaries of the highest graft density, and the cystic structure is indicated with a black arrow. To the left of the cystic structure, just caudal to the indicated graft boundary, residual cavitation is apparent (FIG. 6B). The cystic structure was comprised of human cells based on positive labeling with a human Alu DNA repeat sequence probe (brown nuclear signal, eosin counterstain (FIG. 6C). Few Ki-67-positive cells were detectable by immunohistochemistry within the injury/graft site or within the cystic structure (FIG. 6D). Myelinated fibers labeled with Eriochrome cyanine (blue) were detectable within the injury/graft site and immediately adjacent to the cystic structure (FIG. 6E).

In 6 of the 252 animals injected with AST-OPC1, small "cystic-like epithelial structures" were observed. Of the 6 observed instances of cyst formation, 2 were observed in animals that received a dose of $2.4\times10^5$ AST-OPC1 and 4 were observed in animals that received a dose of $2.4\times10^6$ AST-OPC1. These cystic structures were confined to the lesion site, ranged in size from 34-980 μm in diameter and were smaller than typical parenchymal cavitation seen in vehicle controls. In 3 of these 6 animals, 2-3 separate cystic structures were observed in close proximity to one another in the histological sections and may have represented lobules of a single structure. A thoracic spinal cord tissue section containing one of these cystic structures is shown in FIG. 6A. Cystic structures were lined with cells exhibiting epithelial morphology (FIG. 6B), were of human origin (FIG. 6C), and were not highly proliferative given that very few cells were positive for the proliferative marker, Ki67 (FIG. 6D). Cystic structures were never observed in healthy tissue or in the cervical spinal cord or brain of any animal in the study. There were no apparent clinical symptoms in the animals in which cystic structures were observed.

Example 7

Additional Teratoma Assessments of AST-OPC1

The potential for teratoma formation by AST-OPC1 was also tested in the spinal cord of CB-17/IcrCrl-Prkdc$^{scid}$ Lyst$^{bg}$BR (SCID/bg) mice at 12 months post-administration for two different lots of AST-OPC1. In these studies, $2\times10^6$ AST-OPC1 were administered to the intact, uninjured T10 thoracic spinal cord of the immunocompromised mice. A positive control group received undifferentiated hESCs, and a negative control group received HBSS vehicle alone. Additional treatment groups received a total of $2\times10^6$ cells containing AST-OPC1 spiked with 1, 5, 10, or 50% undifferentiated hESCs. Treatment groups consisted of equal number of males and females and were followed for 12 months to assess tissues for teratoma or any other tumor formation. Animals euthanized prior to 12 month follow-up were also examined at termination for teratoma formation. ISH with hAlu was performed for all recovered spinal cords and confirmed that human AST-OPC1 persisted in >97% of animals.

Figures 7A, 7B:
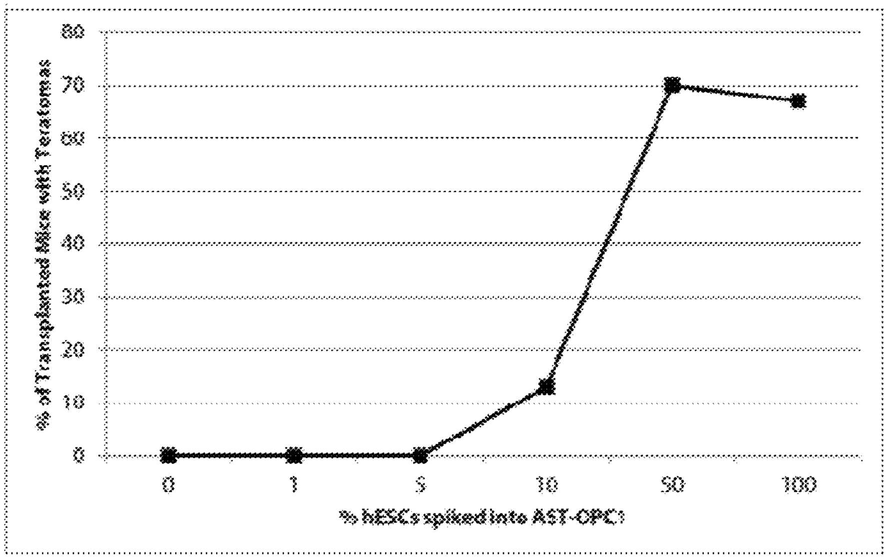
FIG. 7A and FIG. 7B depict frequency of teratoma formation in mice treated with AST-OPC1 or AST-OPC1 spiked with increasing levels of undifferentiated hESCs.
Figures 8A, 8B, 8C, 8D:
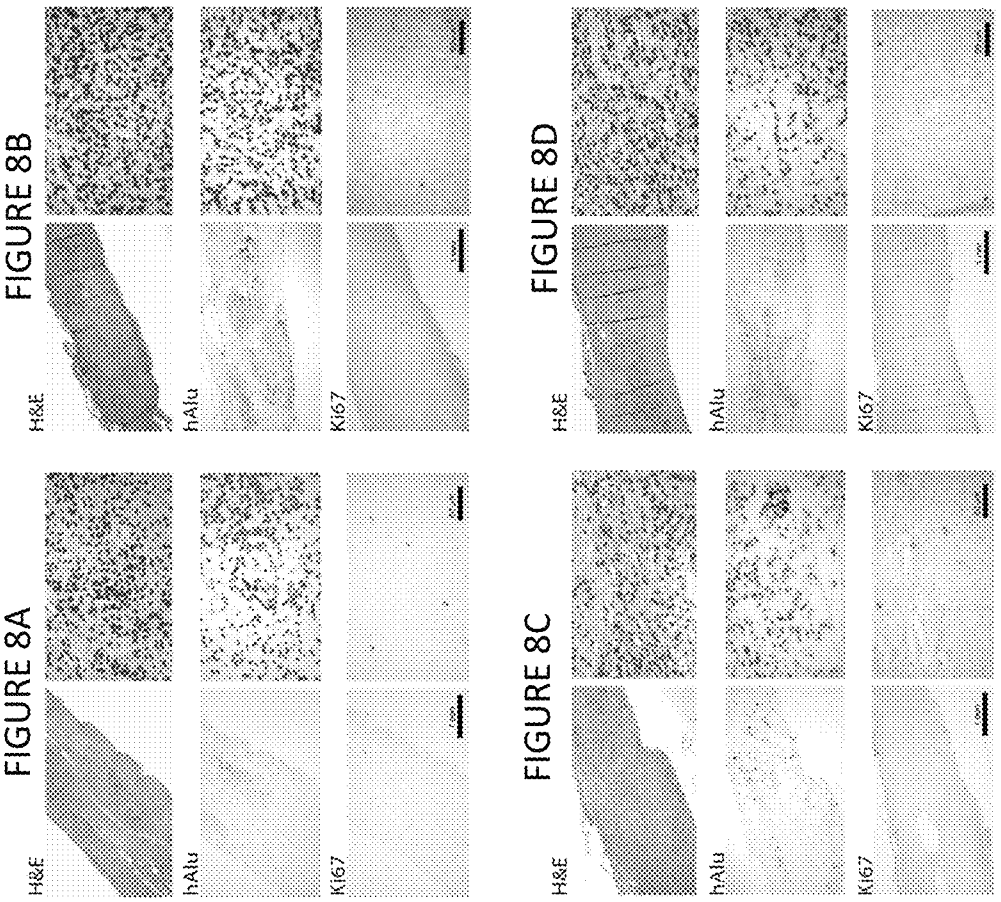
FIGS. 8A-8D depict representative histology of rat thoracic spinal cord 9 months after contusion injury and AST-OPC1 transplantation. Each of the FIGS. 8A-8D corresponds to a different animal.

No teratomas were observed in mice that were injected in the uninjured spinal cord with vehicle alone. Nine of 20 (45%) of these vehicle control animals survived to the 12 month termination point. By contrast, teratomas were observed in the majority of animals injected with 100% undifferentiated hESCs. In these animals, 20 of the 30 (67%) mice injected with $2\times10^6$ undifferentiated hESCs developed teratomas in the spinal cord (FIG. 7). Only 6 of the 30 (20%) animals survived to the 12 month termination point. None of the 128 mice injected with $2\times10^6$ AST-OPC1 and examined histologically showed any evidence of teratomas and 51% survived throughout the 12 month in life phase. In addition, AST-OPC1 spiked with 50% undifferentiated hESCs produced teratomas in approximately 70% of mice. With lower numbers of undifferentiated hESCs, the frequency of teratoma formation decreased. Only 13% (4 of 31) mice receiving AST-OPC1 spiked with 10% hESCs produced teratomas, whereas AST-OPC1 spiked with 5% and 1% undifferentiated hESC did not lead to teratoma or tumor formation (0 of 12 and 0 of 36, respectively).

Example 8

Phase I Thoracic Spinal Cord Injury Clinical Trial of AST-OPC1 Cells

Subjects with neurologically complete, subacute spinal cord injuries (SCI) were recruited in an open-label, multicenter safety study of AST-OPC1 cells. The main inclusion criteria were a traumatic, non-penetrating SCI with single neurological level from T3-T10. Potential subjects had to provide informed consent from 3 to 11 days after their injury so that AST-OPC1 could be administered 7-14 days after SCI. In addition, prospective participants were required to provide consent for both a primary protocol, under which they were followed for one year, and for a long-term follow-up protocol, under which they will be followed for an additional 14 years.

Five eligible subjects received a single dose of $2\times10^6$AST-OPC1 cells in a dedicated surgical procedure for the study. The cells were administered via direct injection to the spinal cord approximately 5 mm caudal to the lesion epicenter using a syringe positioning device specifically designed for this purpose. Subjects received a low dose of tacrolimus (initially 0.03 mg/kg/day PO, then adjusted to maintain a trough blood level of 3-7 ng/mL) which was tapered at day 46 and discontinued at day 60. The primary endpoint of the study was safety with the secondary endpoint being neurological function. Safety was assessed with respect to AST-OPC1 itself, the procedure to deliver the cell product and the transient immunosuppression used subsequent to implantation. All five subjects who received AST-OPC1 in the primary protocol were enrolled in the long-term follow-up protocol.

The study incorporated multiple safety assessments and procedures including: frequent neurological exams, frequent standardized ISNCSCI (International Standards for Neurological Classification of Spinal Cord Injury) exams, serial MRI scans of the spine and brain, stopping rules for precertified safety concerns, and real time notification of an independent Data Monitoring Committee (DMC) for prespecified safety concerns.

Safety results. Both AST-OPC12 cells and the immunosuppression regime were well tolerated. There were no serious adverse events (SAEs) associated with AST-OPC1 either during the primary protocol or during the long-term follow-up. A total of three SAEs (pyelonephritis, Grade 2; urinary tract infection, Grade 3; and autonomic dysreflexia/dyspnea, Grade 3) were reported, none of which were considered to be associated with AST-OPC1, injection procedure or immunosuppression. Adverse events possibly associated with AST-OPC1 included transient low grade fever (1 incident) and neuralgia/burning sensation in trunk and lower extremities (4 incidents in one subject). Additionally, there were 16 incidents of grade 1 or 2 adverse events possibly associated with immunosuppression, including nausea, urinary tract infection and low magnesium blood levels.

Magnetic resonance imaging (MRI) data. Serial MRI scans of the entire spinal cord (visualized on scans of the cervical and thoracic spine) were obtained at screening and at 7, 30, 90, 120, 180, 270 and 365 days after AST-OPC1 injection. MRI scans of the brain were also obtained at screening and at selected postoperative time points. The subjects continued (and still continue) to have annual MRI scans of the brain and spinal cord under the long-term follow-up protocol. Under the primary protocol, no subject exhibited evidence of an enlarging cyst, enlarging mass, spinal cord damage related to the injection procedure, intramedullary hemorrhage, cerebrospinal fluid (CSF) leak, epidural abscess or infection, inflammatory lesions of the spinal cord, CSF flow obstruction, or masses in the ventricular system.

In addition to the MRI readouts focused on potential safety related issues (described above), an additional review of the scans was conducted to assess lesion site parenchymal cavitation and the potential activity of AST-OPC1 cells.

Potential activity of AST-OPC1 cells may be demonstrated by the presence of tissue in place of the lesion cavities in study subjects.

The lesion site parenchymal cavitation review focused on the MRI axial and sagittal T1, T2, and STIR sequences for each subject. Time points included the baseline MRI scans, selected scans during the first year of follow up, the scan at day 365 (i.e. Year 1) visit, and all subsequent scans during the long-term follow-up to date.

Figure 12B:
FIG. 12A and FIG. 12B depict sagittal (FIG. 12A) and axial (FIG. 12B) MRI scans on T2 thoracic vertebra in a clinical trial subject at 3 years after administration of $2\times10^6$ AST-OPC1 to the subject. The images are representative of 4 of the 5 enrolled clinical trial subjects.
Figure 12A:
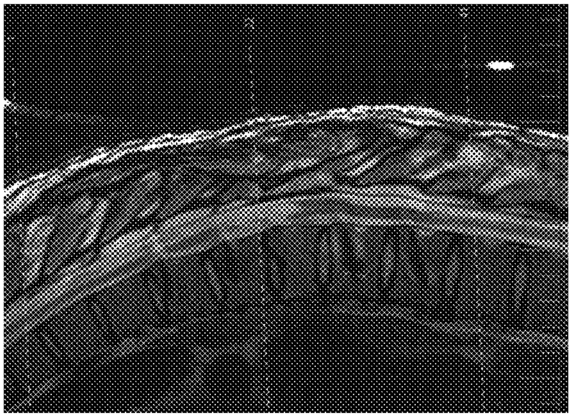

Significant variability in lesion severity and morphology between subjects was noted on MRI, despite the fact that clinically all subjects were American Spinal Injury Association (ASIA) Impairment scale Grade A. In all subjects, the rostral and caudal lesion margins were sharply demarcated on sagittal images by Day 90 and were stable thereafter. In 4 of 5 subjects, the lesion/graft sites were hyperintense on the T2-weighed images at later time points (commencing at Day 180 and up to Year 4, which is the latest time point data currently available for 4 out of 5 subjects), with the signal intensity less than that of cerebrospinal fluid (FIG. 12A and FIG. 12B). This is consistent with the presence of viable graft tissue in the lesion site (Wirth, E D 3r[d], Theele D P, Mareci T H, Anderson D K, Reier P J. Dynamic assessment of intraspinal neural graft survival using magnetic resonance imaging. *Exp Neurol.* 1995 November: 136(1): 64-72), although it is possible that graft tissue could be mixed with some residual host tissue, scar tissue, and/or microcysts. The lesion/graft site signal intensity was similar to cerebrospinal fluid in the remaining subject, suggesting lack of viable graft tissue in the lesion site. Overall, these data support prevention or reduction of lesion cavity formation in four of the five subjects during both the one year primary protocol and the long-term follow-up protocol. Parenchymal cavitation may have been substantially prevented or reduced by the formation of a tissue matrix in the lesion site.

TABLE 2

Summary of spinal cord MRI findings during initial and long-term follow-up of five subjects with neurologically complete, subacute thoracic SCI that received an injection of 2 × $10^6$ AST-OPC1 cells.

| MRI scan date | T2 sagittal | T2 axial |
|---|---|---|
| Day 30 | 5/5 spinal cord edema consistent with subacute SCI<br>5/5 no adverse findings as a result of OPC1 injection | 5/5 spinal cord edema consistent with subacute SCI<br>5/5 no adverse findings as a result of OPC1 injection |
| Day 90 | 4/5 - edema gone or nearly gone with no evidence of a cystic lesion cavity forming<br>1/5 - lesion is uniformly bright with intensity similar to cerebrospinal fluid (CSF) | 4/5 - edema gone or nearly gone with no evidence of a cystic lesion cavity forming<br>1/5 - lesion is uniformly bright with intensity similar to CSF |
| Day 180 | 4/5 subjects - hyperintense, intensity less than that of CSF (consistent with presence of viable graft tissue and reduced cavitation)<br>1/5 subject - signal intensity similar to CSF (consistent with no viable graft tissue) | 4/5 subjects - hyperintense, intensity less than that of CSF (consistent with presence of viable graft tissue and reduced cavitation)<br>1/5 subject - signal intensity similar to CSF (consistent with no viable graft tissue) |
| Year 1 | 4/5 - hyperintense<br>1/5 - signal intensity similar to CSF | 4/5 - hyperintense<br>1/5 - signal intensity similar to CSF |
| Year 2 | 4/5 - hyperintense<br>1/5 - signal intensity similar to CSF | 4/5 - hyperintense<br>1/5 - signal intensity similar to CSF |
| Year 3 | 4/5 - hyperintense<br>1/5 - signal intensity similar to CSF | 4/5 - hyperintense<br>1/5 - signal intensity similar to CSF |
| Year 4 | 4/5 - hyperintense<br>1/5 - signal intensity similar to CSF | 4/5 - hyperintense<br>1/5 - signal intensity similar to CSF |

Immunological assessment of AST-OPC1 graft rejection. The one year primary protocol included collection of cerebrospinal fluid (CSF) and peripheral blood to evaluate whether the subjects mounted an adaptive immune response specific to AST-OPC1 and to monitor for evidence of CNS inflammation at the time of tacrolimus discontinuation. CSF was collected via lumbar puncture immediately prior to surgery for AST-OPC1 injection and at Day 60. Peripheral blood was collected at baseline and at frequent intervals through one year follow-up. Additional blood samples were collected under the long-term follow-up protocol.

The immune monitoring assays were designated as exploratory assessments under the one year primary protocol and the long-term follow-up protocol. Serum and CSF from the subjects were assessed for the possible development of antibodies to the specific human leukocyte antigens (HLA) on AST-OPC1 using the FlowPRA® assay (One Lamba, Inc.). Potential development of a cellular immune response to AST-OPC1 was assessed using a mixed lymphocyte reaction (MLR) assay using peripheral blood monocytes (PBMC) from the subject and AST-OPC1. The MLR was detected using the enzyme-linked immunosorbent spot (ELISPOT) assay for lymphocyte production of interferon-gamma (IFN-γ).

Figure 13:
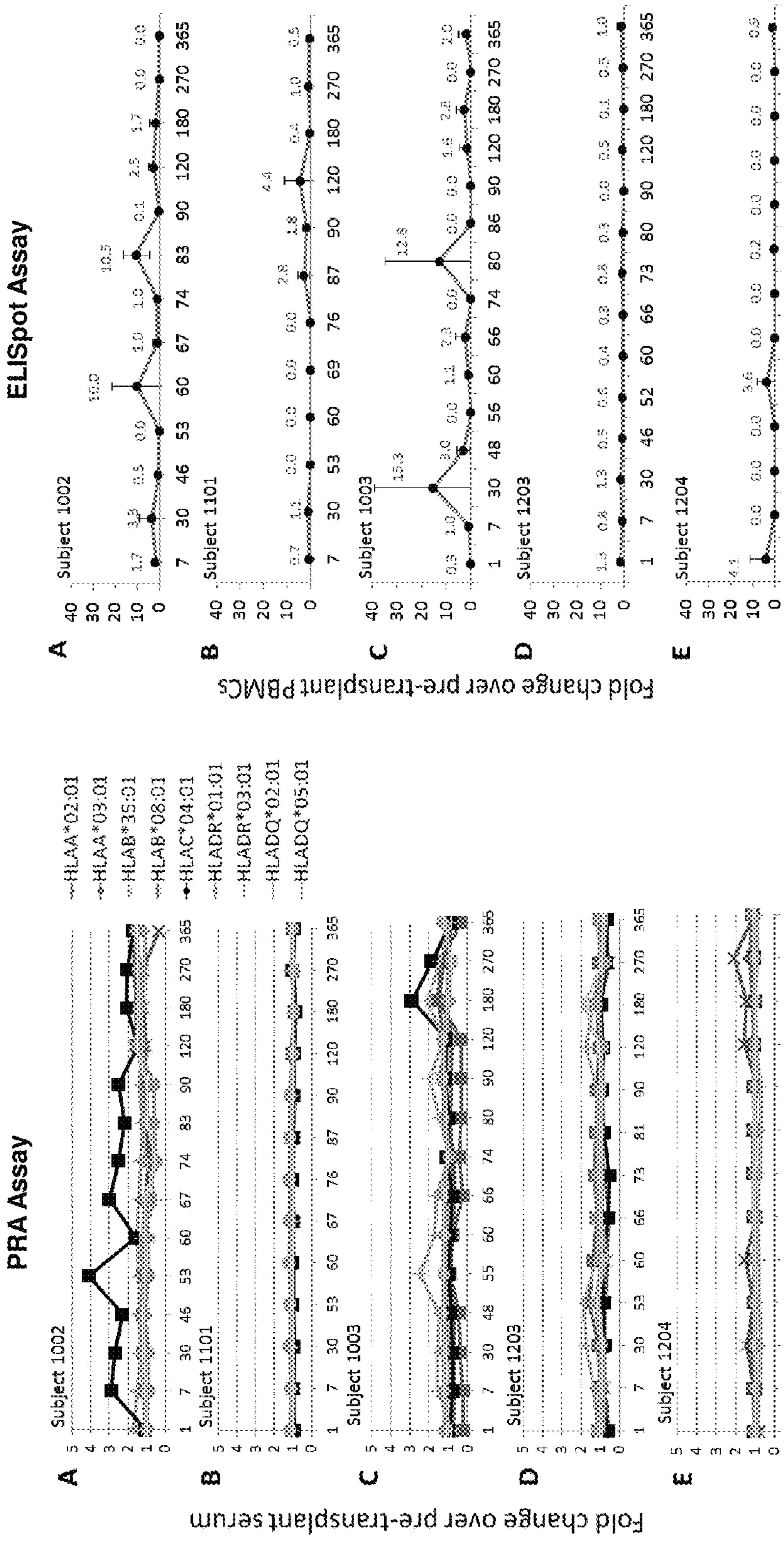
FIG. 13 depicts the results of immune monitoring assays in the 5 clinical trial subjects at successive time points up to one year post-grafting.

Study results revealed that there were no observed increases in T cell mediated responses against AST-OPC1 that were sustained at successive time points post-transplant for any of the 5 subjects tested (FIG. 13). There were no sustained increases in serum HLA-DSA (donor specific antibodies) from all 5 subjects tested.

In conclusion, based on the results from the immune monitoring assays, there was no detection of humoral or cellular immune responses against AST-OPC1 that were sustained at successive time points through 1 year of follow-up.

Efficacy results. No subjects exhibited evidence of major sensory neurological improvement or deterioration through year 2 of follow-up. (FIG. 14). Given the low dosage of AST-OPC1 cells administered in the first clinical study, lack of detectable improvement in sensory neurological function was expected.

Example 9

Quantification of Parenchymal Cavitation at the Contusion/Injury Site in Cervical Spinal Cord Injury Contusion site parenchymal cavitation was assessed and quantitated in rats with cervical spinal cord injury.

Athymic nude rats [Crl:NIH-Foxn1rnu] received a 150 kdyne contusion injury at C5 using the Infinite Horizons Impactor (Precision Systems & Instrumentation, Fairfax, Va.) and were implanted with 2×$10^6$ AST-OPC1 cells or HBSS vehicle control at 6-9 days post-injury. Nine months post-implantation, the lesion sites were examined histologically and the results were quantitated.

To examine the anatomical effects of AST-OPC1 transplantation on progression of the secondary injury contusion cavity, spinal cord tissue was cut on the longitudinal (horizontal) plane to allow visualization of the rostrocaudal extent of the injury site and the grafted AST-OPC1 cells.

Contusion site cavitation measurements were performed blind with respect to treatment group on horizontal sections of spinal cord processed for Hematoxylin and Eosin staining. Stained sections encompassing the injury area and graft were imaged at 2.5× magnification using a Zeiss Axioskop 2 Plus microscope (Carl Zeiss, Göttingen, Germany). One representative spinal cord tissue section near the level of the central canal from each animal was chosen for measurements of cavitation area. Measurements were performed using Image J software (U.S. National Institutes of Health, Bethesda, Md.) to manually trace the perimeter of each area of cavitation within the contusion injury site. The initial measurement output in pixels was converted to millimeters, such that the total cavitation area for each animal was expressed in units of square millimeters. Scatter plots of individual cavitation area measurements, as well as the mean cavitation area and standard error of the mean (SEM) was calculated for each treatment group and displayed graphically using JMP software (V 11.0.0, SAS Institute, Inc., Cary, N.C.).

To identify myelinated fibers with the spinal cord, tissues were stained with Eriochrome (Solochrome) cyanine solution, followed by differentiation in 10% iron alum. Slides were counterstained with Ruben's Eosin-Phloxine (Biocare Medical, Concord, Calif.), dehydrated through a sequential ethanol series, cleared with xylenes and coverslipped with EcoMount (Biocare Medical, Concord, Calif.).

Figure 15A:
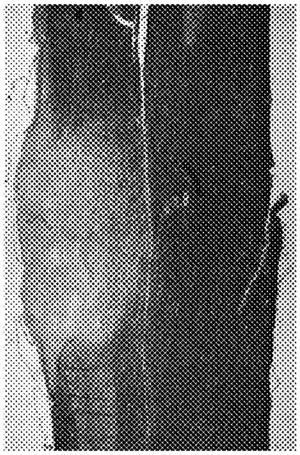
FIGS. 15A-15C depict AST-OP1 prevention of parenchymal cavitation in rats with cervical spinal cord contusion injury.
Figure 15B:
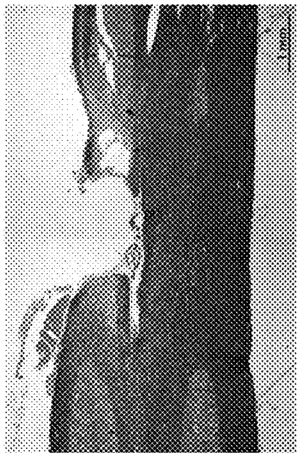
Figure 15C:
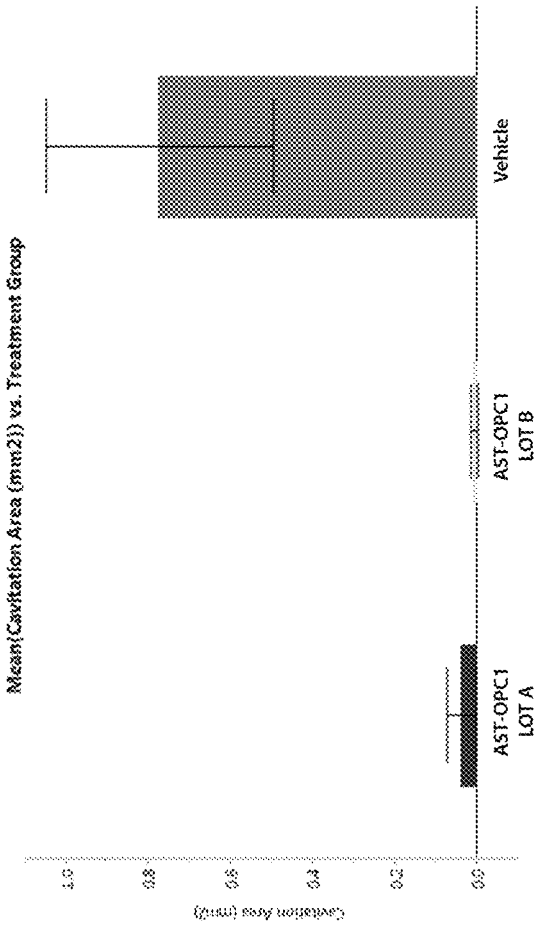

Consistent with our previous studies in which spinal cord contusion and AST-OPC1 transplantation occurred at the thoracic level, the parenchymal cavitation that is expected secondary to a contusion injury was not observed in majority of animals that received AST-OPC1 (compare examples of cavitation in HBSS-treated animals, FIG. 15B, versus reduced cavitation in AST-OPC1-treated animals, FIG. 15A). While cavity formation was not prevented in all animals that received AST-OPC1, parenchymal cavitation was not observed in 124 of 129 animals that received AST-OPC1 and were assessed for micropathology. Of the 62 animals that received AST-OPC1 Lot A, two animals had measureable areas of injury-induced parenchymal cavitation (3%), and of the 67 animals that received AST-OPC1 Lot B and were assessed for micropathology, three animals had measureable areas of injury-induced parenchymal cavitation (4%). In contrast, 7 of 12 animals that received HBSS vehicle had measurable parenchymal cavitation at the injury site (58%). In addition, of the animals with measureable cavitation at the injury site, the average cavitation area was reduced in animals treated with AST-OPC1relative to those treated with HBSS (mean cavitation area±standard deviation: AST-OPC1=0.64±0.88 mm2; HBSS=1.33±0.91 mm2). The overall mean cavitation areas are shown for each treatment group in FIG. 15C.

What is claimed is:

1. A method of reducing spinal cord injury-induced parenchymal cavitation in a human subject with an acute spinal cord injury, the method comprising directly injecting into the spinal cord injury site approximately 5 mm caudal of the spinal cord injury epicenter of said subject a composition comprising a population of human pluripotent stem cell-derived oligodendrocyte progenitor cells (OPCs) that are capable of engrafting at the spinal cord injury site and remaining within the spinal cord injury site of said subject for a period of 180 days or longer following the injection.

2. The method according to claim 1, further comprising administering to the subject a low dose immunosuppressant regimen.

3. The method according to claim 2, wherein the immunosuppressant regimen comprises a tacrolimus dose of about 0.03 mg/kg/day per os, adjusted to maintain a trough blood concentration of about 3-7 ng/ml through about day 46 following the administering of the composition comprising a population of allogeneically derived OPCs, followed by tapering off and discontinuing the immunosuppressant regimen at about day 60 following the administering of the composition.

4. The method according to claim 1, wherein the OPCs are capable of remaining within the spinal cord injury site of said subject for a period of about 2 years or longer following the injection of the composition to the spinal cord injury site.

5. The method according to claim 1, wherein the OPCs are capable of remaining within the spinal cord injury site of said subject for a period of about 3 years or longer following the injection of the composition to the spinal cord injury site.

6. The method according to claim 1, wherein the OPCs are capable of forming a tissue matrix in the spinal cord injury site of said subject within about 180 days or less, thereby reducing spinal cord injury-induced parenchymal cavitation.

7. The method according to claim 1, wherein the subject has a thoracic or cervical spinal cord injury.

8. The method according to claim 1, wherein the composition comprises between about $2\times10^6$ and $50\times10^6$ AST-OPC1 cells.

9. The method of claim 1, wherein the oligodendrocyte progenitor cells are derived from human embryonic stem (hES) cells.

10. The method of claim 1, wherein the oligodendrocyte progenitor cells are derived from induced pluripotent stem (iPS) cells.

* * * * *